(12) United States Patent
Remus et al.

(10) Patent No.: US 11,794,976 B2
(45) Date of Patent: Oct. 24, 2023

(54) RECYCLABLE ABSORBENT ARTICLE PACKAGE MATERIAL

(71) Applicant: The Procter & Gamble Company, Cincinnati, OH (US)

(72) Inventors: Michael Remus, Schwalbach am Taunus (DE); Edward Daniel Theiss, III, Union Township, OH (US); Michael Wayne Taylor, Cincinnati, OH (US); Michaela Monika Czupik, Cincinnati, OH (US); Emily Charlotte Boswell, Cincinnati, OH (US); Benjamin Jacob Clare, Cincinnati, OH (US); Patti Jean Kellett, Cincinnati, OH (US); Peter Kramkowski, Schwalbach am Taunus (DE); Ilana Jessica Krause, Cincinnati, OH (US); Lee Matthew Arent, Fairfield, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 55 days.

(21) Appl. No.: 17/389,391

(22) Filed: Jul. 30, 2021

(65) Prior Publication Data
US 2022/0033159 A1    Feb. 3, 2022

Related U.S. Application Data

(60) Provisional application No. 63/089,580, filed on Oct. 9, 2020, provisional application No. 63/058,516, filed
(Continued)

(51) Int. Cl.
*B65D 75/20* (2006.01)
*B65D 85/07* (2017.01)
(Continued)

(52) U.S. Cl.
CPC ............. *B65D 75/20* (2013.01); *B65D 65/14* (2013.01); *B65D 65/38* (2013.01); *B65D 85/07* (2018.01); *B65D 2565/385* (2013.01)

(58) Field of Classification Search
CPC ........ B65D 75/20; B65D 85/07; B65D 65/14; B65D 65/38; B65D 2565/385
(Continued)

(56) References Cited

U.S. PATENT DOCUMENTS 2,146,308 A   2/1939   Maxfield
2,290,564 A   7/1942   Krueger
(Continued)

FOREIGN PATENT DOCUMENTS

| EP | 1291290 A1 | 3/2003 |
| EP | 1618860 A1 | 1/2006 |
| EP | 2276673 B1 | 1/2014 |
| EP | 2730698 A1 | 5/2014 |
| EP | 2796384 A1 | 10/2014 |
| EP | 2704963 B1 | 9/2016 |

(Continued)

OTHER PUBLICATIONS

Axello Tough White White MF Kraft Paper. Specification Data [online]. BillerudKorsnas Axello, Sep. 12, 2019 [retrieved on Sep. 22, 2022]. Retrieved from the Internet :https://www.billerudkorsnas.com/packaging-materials/kraft-paper-bags/axello (Year:2019).
(Continued)

*Primary Examiner* — Jacob K Ackun
(74) *Attorney, Agent, or Firm* — Amanda Herman Berghauer; George Henry Leal

(57) ABSTRACT

A package of one or more absorbent articles is disclosed. The package has a package material including natural fibers. The package has a plurality of panels, including a consumer-facing panel, and wherein the package is sealed such that the one or more absorbent articles are completely enclosed therein. The package material has a basis weight of between 50 gsm to 120 gsm, between 60 gsm to 105 gsm or between
(Continued)

70 gsm to 90 gsm, as determined via ISO 536 as modified herein. The package material is recyclable.

22 Claims, 18 Drawing Sheets

Related U.S. Application Data on Jul. 30, 2020, provisional application No. 63/091,507, filed on Oct. 14, 2020.

(51) Int. Cl.
    *B65D 65/14*     (2006.01)
    *B65D 65/38*     (2006.01)

(58) Field of Classification Search
    USPC .......................................... 206/494
    See application file for complete search history.

(56) References Cited

U.S. PATENT DOCUMENTS

| | | |
|---|---|---|
| 2,821,337 A | 1/1958 | Morgan, Jr. |
| 3,312,339 A | 4/1967 | Million |
| 3,462,026 A | 8/1969 | MacCherone |
| 3,519,197 A | 7/1970 | Campbell |
| 3,640,450 A | 2/1972 | Lieberman |
| 3,741,778 A | 6/1973 | Rowe |
| 3,979,049 A | 9/1976 | Achelpohl |
| 4,988,332 A | 1/1991 | Mattle |
| 5,065,868 A * | 11/1991 | Cornelissen ............ B65D 33/02 206/83.5 |
| 5,457,944 A | 10/1995 | Lipes |
| 5,468,206 A | 11/1995 | Buchanan |
| 5,830,118 A | 11/1998 | Nicholson |
| 5,908,113 A | 6/1999 | Takemasa et al. |
| 5,934,470 A * | 8/1999 | Bauer ................ B65D 71/066 206/497 |
| 6,026,957 A * | 2/2000 | Bauer ................ B65D 71/0085 229/87.01 |
| 6,033,112 A | 3/2000 | Sorenson et al. |
| 6,229,061 B1 * | 5/2001 | Dragoo ................ A61F 13/493 604/385.14 |
| 6,446,796 B1 | 9/2002 | Schmidt |
| 6,698,928 B2 | 3/2004 | Miller |
| 7,004,320 B1 | 2/2006 | Schmidt et al. |
| 7,721,887 B2 | 5/2010 | Hancock-Cooke et al. |
| 7,780,353 B2 | 8/2010 | Yoffe |
| 8,074,801 B2 | 12/2011 | Slayton et al. |
| 8,097,313 B2 | 1/2012 | Wallat |
| 8,240,915 B2 | 8/2012 | Sargin et al. |
| 8,348,916 B2 | 1/2013 | Fujikawa et al. |
| 8,631,939 B2 | 1/2014 | Benson et al. |
| 8,794,443 B2 | 8/2014 | Ueda |
| 9,382,043 B2 | 7/2016 | Rummo |
| 9,468,566 B2 | 10/2016 | Rosati et al. |
| 9,878,839 B2 | 1/2018 | Santos |
| 9,914,562 B2 | 3/2018 | Fox et al. |
| 9,932,149 B2 | 4/2018 | Puccini |
| 9,994,376 B2 | 6/2018 | De Soto-burt et al. |
| 10,378,152 B2 | 8/2019 | Kinast |
| 10,760,219 B2 | 9/2020 | Niemi |
| 10,786,404 B2 | 9/2020 | Cheng et al. |
| 11,396,170 B2 | 7/2022 | Knauf et al. |
| 11,420,784 B2 | 8/2022 | Parker et al. |
| 2001/0056270 A1 | 12/2001 | Mizutani et al. |
| 2004/0238393 A1 * | 12/2004 | Ohi ..................... A61F 13/5611 604/385.02 |
| 2004/0241359 A1 | 12/2004 | Miksic et al. |
| 2006/0051603 A1 | 3/2006 | Cleveland et al. |
| 2009/0084698 A1 * | 4/2009 | Ito ..................... A61F 13/5511 604/385.03 |
| 2009/0249751 A1 | 10/2009 | Hyttel et al. |
| 2010/0150479 A1 | 6/2010 | Smith |
| 2010/0273377 A1 | 10/2010 | Files et al. |
| 2011/0046591 A1 * | 2/2011 | Warner ................. B41F 5/18 206/440 |
| 2011/0257616 A1 | 10/2011 | Lakso et al. |
| 2012/0288693 A1 | 11/2012 | Stanley et al. |
| 2013/0046271 A1 | 2/2013 | Pittet et al. |
| 2013/0156352 A1 | 6/2013 | Koehn |
| 2014/0319003 A1 | 10/2014 | Hawighorst et al. |
| 2014/0348445 A1 | 11/2014 | Siesto Casanova et al. |
| 2015/0266663 A1 | 9/2015 | Joseph |
| 2017/0057721 A1 | 3/2017 | Lee et al. |
| 2017/0274613 A1 | 9/2017 | Stafford, III |
| 2018/0289564 A1 | 10/2018 | Sheehan |
| 2018/0304607 A1 | 10/2018 | Öhman et al. |
| 2018/0334292 A1 | 11/2018 | Tan |
| 2019/0091077 A1 | 3/2019 | Cheng et al. |
| 2019/0135515 A1 | 5/2019 | Jasso |
| 2020/0030162 A1 | 1/2020 | Lindner et al. |
| 2020/0354129 A1 | 11/2020 | Sheehan et al. |
| 2021/0043023 A1 | 2/2021 | Coder et al. |
| 2021/0108371 A1 | 4/2021 | Oshima et al. |
| 2021/0114789 A1 | 4/2021 | Kuiper et al. |
| 2021/0221544 A1 | 7/2021 | Wallenius et al. |
| 2022/0031531 A1 | 2/2022 | Remus et al. |
| 2022/0031532 A1 | 2/2022 | Remus et al. |
| 2022/0079819 A1 | 3/2022 | Houben et al. |
| 2022/0110801 A1 | 4/2022 | Remus et al. |
| 2022/0110802 A1 | 4/2022 | Remus et al. |
| 2022/0204234 A1 | 6/2022 | Chapjian |
| 2022/0266563 A1 | 8/2022 | Schlarp et al. |
| 2022/0362073 A1 | 11/2022 | Shimizu et al. |

FOREIGN PATENT DOCUMENTS

| | | |
|---|---|---|
| EP | 3561178 A1 | 10/2019 |
| EP | 3575233 B1 | 3/2021 |
| EP | 3643634 B1 | 7/2021 |
| EP | 3865421 A1 | 8/2021 |
| EP | 3954535 A1 | 2/2022 |
| EP | 3901054 B1 | 8/2022 |
| EP | 4070929 A1 | 10/2022 |
| GB | 823855 A | 11/1959 |
| GB | 829215 A | 3/1960 |
| GB | 1520492 A | 8/1978 |
| GB | 2545456 A | 6/2017 |
| KR | 20080111808 A | 12/2008 |
| NZ | 264733 A | 4/1997 |
| WO | 9210412 A1 | 6/1992 |
| WO | 9723186 A1 | 7/1997 |
| WO | 02094678 A1 | 11/2002 |
| WO | 02096331 A2 | 12/2002 |
| WO | 2004103841 A1 | 12/2004 |
| WO | 2011073808 A2 | 6/2011 |
| WO | 2013008938 A1 | 1/2013 |
| WO | 2013160199 A1 | 10/2013 |
| WO | 2015088037 A1 | 6/2015 |
| WO | 2019056351 A1 | 3/2019 |
| WO | 2020121160 A1 | 6/2020 |
| WO | 2021165317 A1 | 8/2021 |
| WO | 2021172006 A1 | 9/2021 |
| WO | 2021172075 A1 | 9/2021 |
| WO | 2021199600 A1 | 10/2021 |
| WO | 2021199712 A1 | 10/2021 |
| WO | 2021200656 A1 | 10/2021 |
| WO | 2021200657 A1 | 10/2021 |
| WO | 2022022884 A1 | 2/2022 |
| WO | 2022024591 A1 | 2/2022 |
| WO | 2022059324 A1 | 3/2022 |
| WO | 2022129674 A1 | 6/2022 |
| WO | 2022158102 A1 | 7/2022 |

OTHER PUBLICATIONS

Axello Tough White White MF Kraft Paper. Technical Datasheet [online]. BillerudKorsnas Axello, Sep. 12, 2019 [retrieved on Jul. 27, 2022]. Retrieved from the Internet: https://www.billerudkorsnas.com/packaging-materials/kraft-paper-bags/axello (Year: 2019).

(56) References Cited

OTHER PUBLICATIONS

15893MQ PCT Search Report and Written Opinion for PCT/US2021/043815 dated Nov. 11, 2021, 14 pages.
All Office Actions; U.S. Appl. No. 17/389,396, filed Jul. 30, 2021.
All Office Actions; U.S. Appl. No. 17/389,487, filed Jul. 30, 2021.
Jonathan Fowle et al. "Paper-based flexible packaging", 2003, pp. 91-123.
Mark J. Kirwan, "Paper and Paperboard Packaging Technology ", Available on https://www.booksfree.org/wp-content/uploads/2022/02/paper_and_paperboard_packaging_technology-signed.pdf, 2005, pp. 453.
Richard Coles et al. "Food Packaging Technology", available on https://kasianparto.ir/wp-content/uploads/2022/03/Food-Packaging-Technology.pdf, vol. 5, 2003, pp. 362.
Thorsten Schmidt et al. "Reliability of evaluations for the choice of system solutions at the example of automated order picking systems for bagged goods", May 30, 2014, pp. 14.

* cited by examiner

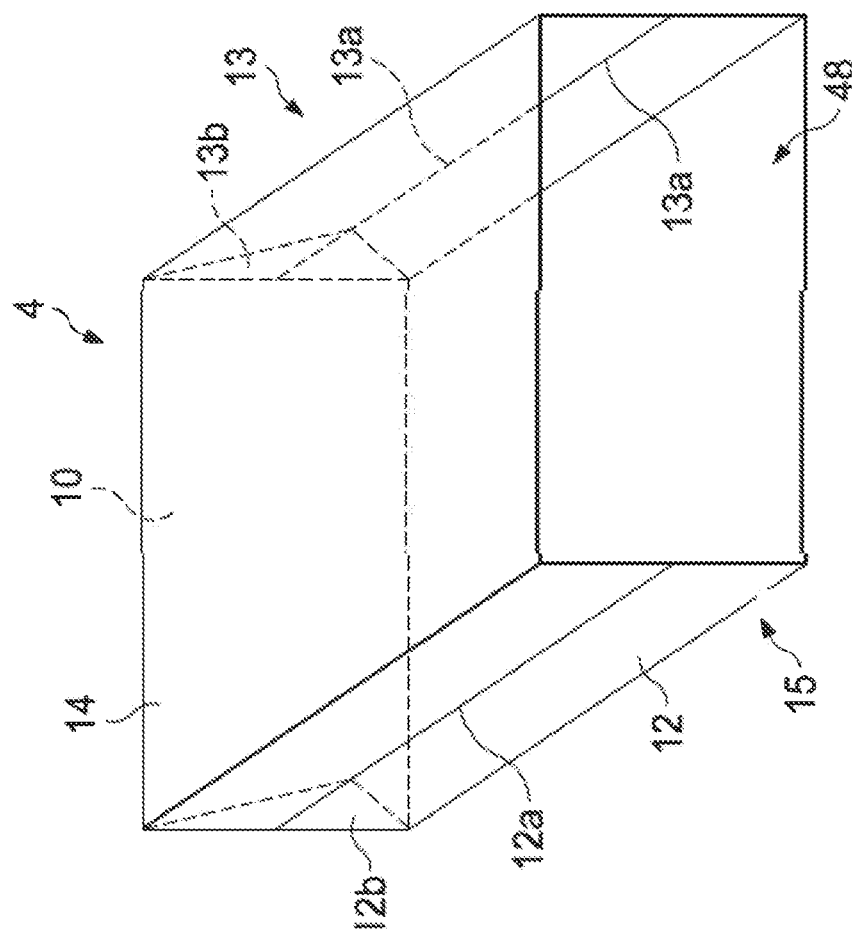

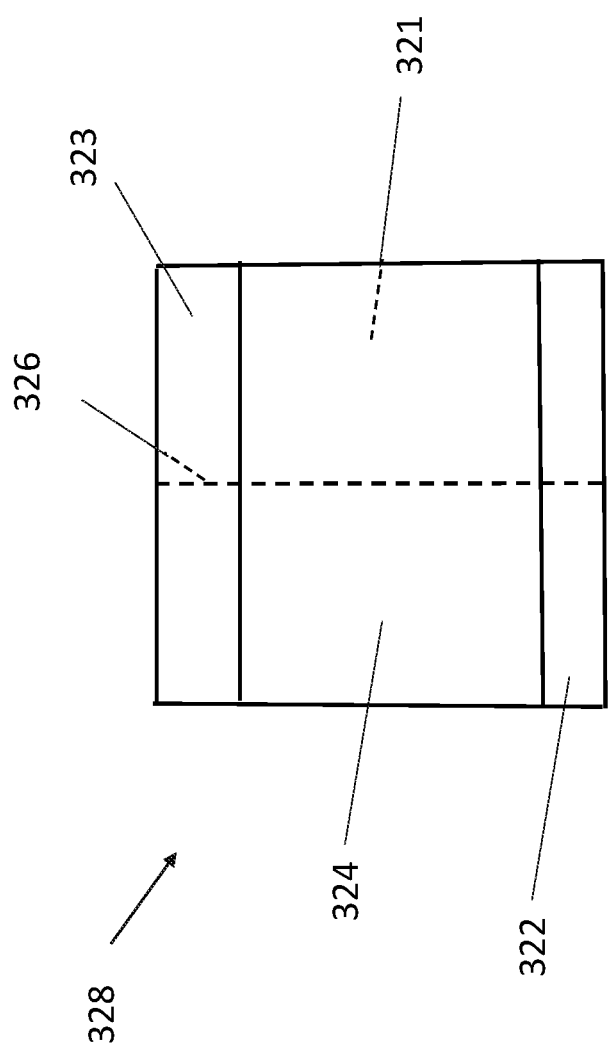

RECYCLABLE ABSORBENT ARTICLE PACKAGE MATERIAL

FIELD OF THE INVENTION

The present invention pertains to disposable absorbent articles and their packaging, more particularly to packaging material for disposable absorbent articles that is recyclable.

BACKGROUND OF THE INVENTION

Products which are environmentally friendly are at the forefront of many consumer's minds at this point in our history. There is an increased focus on products which are sustainably sourced. For example, there is a strong desire in the marketplace to create consumer products which comprise natural materials, bio-sourced materials, and/or recycled materials. On the disposal end, there is an increased focus on products which are bio-degradable, compostable, recyclable, reusable, and/or otherwise cause minimal landfill waste.

In the context of disposable absorbent articles, particularly disposable absorbent article packaging, there are package materials which already satisfy one or both of these criteria. For example, there are a myriad of absorbent articles which utilize carton board as their on shelf package. Carton board, as it is derived from wood pulp, may be one or both sustainably sourced and recyclable. And where the products within the package cannot form a shelf stable surface on their own, carton board is useful.

Where disposable absorbent articles are capable of being compressed and/or forming a shelf stable surface, a more flexible material is often used, i.e. plastic. Plastic is generally preferred over carton board because plastic can withstand the rigors of a packaging process much more so than carton board given the plastic's ability to flex and stretch. However, there is growing public demand for alternatives to plastic and non-plastic based materials. Flexible packaging materials which are natural based would satisfy that demand.

SUMMARY OF THE INVENTION

Packages of the present disclosure comprise one or more absorbent articles therein and comprise a package material comprising natural fibers. Each of the packages comprises a plurality of panels, including a consumer-facing panel, and wherein the package is sealed such that the one or more absorbent articles are enclosed by the package material. Additionally, the packages of the present disclosure are recyclable.

In one embodiment of a package of one or more absorbent articles, the package comprises a package material comprising natural fibers. The package comprises a plurality of panels, including a consumer-facing panel, and wherein the package is sealed such that the one or more absorbent articles are enclosed therein. The package material comprises a basis weight of between 50 gsm to 120 gsm, between 60 gsm to 105 gsm or between 70 gsm to 90 gsm, as determined via ISO 536 as modified herein, and wherein the package material is recyclable.

In another embodiment of a package of one or more absorbent articles, the package comprises a package material comprising natural fibers. The package comprises a plurality of panels, including a consumer-facing panel, wherein at least two of the plurality of panels comprise a seal, such that the one or more absorbent articles are sealed therein. The package material comprises a basis weight of between 50 gsm to 120 gsm, between 60 gsm to 105 gsm or between 70 gsm to 90 gsm, as determined via ISO 536 as modified herein, and the package material is recyclable.

In another embodiment of a package of one or more absorbent articles, the package comprises a package material, comprising natural fibers. The package further comprises a plurality of panels, including a consumer-facing panel, an opposing back panel, a bottom panel, an opposing top panel, and opposing left and right panels. The package comprises a plurality of seals associated with one or more of the plurality of panels. The package material comprises a basis weight of between 50 gsm to 120 gsm, between 60 gsm to 105 gsm or between 70 gsm to 90 gsm, as determined via ISO 536 as modified herein, and the package material is recyclable.

In another embodiment of a package of one or more absorbent articles, the package comprises a package material comprising natural fibers. The package further comprises a plurality of panels, including a consumer-facing panel, an opposing back panel, a bottom panel, an opposing top panel, and opposing left and right panels, wherein at least one of the bottom panel or back panel comprise a seal, wherein at least one of the top panel, left panel, and/or right panel comprise an access seal. The package material comprises a basis weight of between 50 gsm to 120 gsm, between 60 gsm to 105 gsm or between 70 gsm to 90 gsm, as determined via ISO 536 as modified herein, and the package material is recyclable.

BRIEF DESCRIPTION OF THE DRAWINGS

FIG. 1C is a schematic representation of a package in accordance with the present disclosure in an open state.

FIG. 3B is a schematic representation showing another package in accordance with the present disclosure constructed with a flow wrap process.

DETAILED DESCRIPTION OF THE INVENTION

Figure 1A:
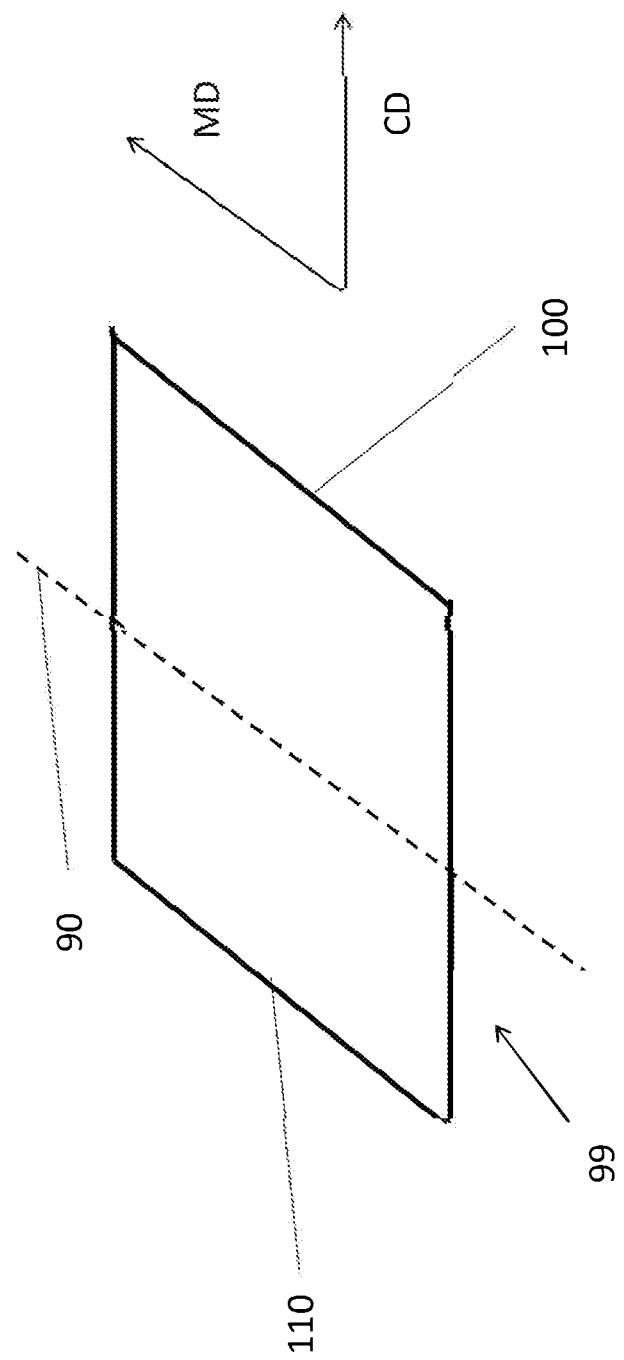
FIG. 1A is a schematic representation of a package material sheet in accordance with the present disclosure.

The term "absorbent article" as used herein refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, diaper outer covers, absorbent inserts for the diaper outer covers, menstrual pads, incontinence pads, liners, pantiliners, tampons, durable menstrual pants, disposable swim pants and the like. Additionally, the term "absorbent article" includes cleaning devices which can be utilized to clean surfaces such as dusting wipes, dusting wipe refills which fit on a re-usable handle, sweeping and/or mopping pads, sweeping or mopping pad refills which can attach to a re-usable handle.

The term "cross-machine direction" or "CD", as used herein, refers to the path that is perpendicular to the machine direction in the plane of the web.

The term "machine direction" or "MD", as used herein, refers to the path that material, such as a web, follows through a manufacturing process.

The term "colorant", as used herein, refers to inks, dyes, pigments, or the like, used to create color in a substrate.

The term "natural fibers" as used herein, refers to fibers which comprise cellulose-based fibers, bamboo based fibers, and the like. Natural fibers also refers to nonwoody fibers, such as cotton, abaca, kenaf, sabai grass, flax, esparto grass, straw, jute hemp, bagasse, milkweed floss fibers, and pineapple leaf fibers; and woody, wood, or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it can be desirable that the natural fibers be relatively undamaged and largely unrefined or only lightly refined. The fibers can have a Canadian Standard Freeness of at least 200, more specifically at least 300, more specifically still at least 400, and most specifically at least 500.

The term "cellulose-based fibers," as used herein, may include cellulose fibers such as wood fiber, cotton, regenerated cellulose fiber such as viscose, lyocell, rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

The terms "non-recyclable material" or "contaminant" as used herein, refers to materials which are believed to be unsuitable for processing in the natural fiber recycling process. However, in alternative recycling streams, the materials provided with one or both of these designations may be recyclable.

The package materials of the present disclosure allow for flexibility for the consumer particularly during disposal. The package materials of the present disclosure can be recycled or composted which minimizes material sent to landfills. Package materials of the present disclosure comprise natural fibers. The package materials of the present disclosure can be processed to form packages comprising one or more absorbent articles.

The package material of the present disclosure can be arranged as a package in a myriad of configurations containing one or more absorbent articles. For example, the package may comprise a plurality of panels, including a consumer-facing panel. The consumer-facing panel is the face of the package, when on shelf, that faces the consumer. In general, the consumer-facing panel comprises branding and/or package information, each of which is described in additional detail herein. Also, each of the plurality of panels comprises an inner surface and an outer surface.

Packages of the present disclosure may comprise a generally cuboid shape. So, in addition to the consumer-facing panel, the packages of the present disclosure may further comprise a back panel opposing the consumer-facing panel, a left panel disposed between the consumer-facing panel and the back panel, a right panel opposing the left panel, a bottom panel disposed between the consumer-facing panel and the back panel, and an opposing top panel.

The package material may be unitary. For example, multiple folds may be utilized to form the plurality of panels of the package. To further elucidate the example where the package is a cuboid shape, at least one fold may be disposed between each of: (1) the consumer-facing panel and the left panel; (2) between the consumer-facing panel and the right panel; (3) between the consumer-facing panel and the top panel; and (4) between the consumer-facing panel and the bottom panel. Additionally, at least one fold may be disposed between each of: (1) the back panel and the left panel; (2) between the back panel and the right panel; (3) between the back panel and the top panel, and (4) between the back panel and the bottom panel.

As an alternative to the foregoing, the packages of the present disclosure may comprise package material which comprises a plurality of discrete portions. Such configurations are described in additional detail herein.

For packages which comprise a cuboid shape, the consumer-facing panel may be positioned generally perpendicular to a store shelf whereas the bottom panel may sit generally flat on the store shelf or atop another package. Generally perpendicular, assuming the store shelf to be perfectly horizontal, means that the consumer-facing panel is within plus or minus 35 degrees of a vertical orientation. Generally flat, again assuming the store shelf to be perfectly horizontal, means that the bottom panel is within plus or minus 35 degrees of a horizontal orientation. Alternatively, the consumer-facing panel, in some configurations, may be oriented generally horizontal to the store shelf and face the consumer as the consumer looks down on the package.

Other package shapes are contemplated. Examples of such packages include flow wrap or horizontal form-fill and seal wrap. Such packages may comprise a generally cuboid shape also configured as described above. However, in some instances, particularly where a low number of absorbent articles are included therein, these packages may comprise a consumer-facing panel and an opposing back panel. In such packages, a hoop seal may be formed, as described herein, as well as end seals. In such configurations, the consumer-facing panel may be oriented generally in a vertical direction or in a generally horizontal direction. Additionally, in such packages, there may be an absence of fold lines which distinguish the consumer-facing panel from the back panel. Instead, there may be a curved surface between these panels.

Additional examples are contemplated where package shapes comprising less than six panels are formed. Building on these examples, packages having a circular or semi-circular shape when viewed from a bottom panel are contemplated. Additionally, packages having a triangular shape when viewed from the bottom panel are contemplated. Regardless of the number of panels comprised by the packages of the present disclosure, the package comprises a consumer-facing panel.

In accommodating one or more absorbent articles, packaging material of the present disclosure, in addition to the natural fibers, may also comprise adhesives, coatings, colorants and/or other materials, e.g. barrier materials. The adhesives and/or the barrier material, e.g. film, may be utilized to create seals in the package material which seal the one or more absorbent articles therein. The creation of seals reduces the likelihood of contamination of the one or more absorbent articles within the package. And, the coatings and/or colorants, may be utilized to provide branding, background color, and/or package information on one or more of the panels. Unfortunately, the addition of adhesives, coatings, colorants and/or other materials, can be seen as non-recyclable materials in the recycling process. The use of adhesives, coatings, colorants and other materials, e.g. barrier materials, are discussed in additional detail hereafter.

It is worth noting that where a barrier material is utilized, the barrier material may be selected such that the use of adhesives can be reduced and possibly eliminated. One suitable example of a barrier material is a polyethylene film which may be coated on an inner surface of the package material. The polyethylene can be utilized to form the seals rather than an adhesive or possibly in conjunction with adhesive.

Additionally, the barrier material may at least partially inhibit the migration of water vapor through the package material. The barrier material may comprise a water soluble material that may not interfere with a recycling process. The barrier material may be easily separable from the remainder of the package materials through a recycling process, for example by having a different water solubility, density, or other physical features as compared to the remainder of the package materials.

However, forms are contemplated where the barrier material comprises a plastic film. In such instances, the weight percentage of the barrier material can impact the recyclability of the package material. For example, where the barrier material comprises a plastic film, the barrier material may be seen as non-recyclable material in the natural fiber recycling process. One example of a plastic film that can be utilized as a barrier material is polyethylene film. However, as noted previously, polyethylene film may obviate the need for adhesive for the creation of the seals of the packages of the present disclosure. Additionally, as the barrier material may not be recyclable in the same stream as the other package materials, the weight percentage of the barrier material may be in accordance with the present description regarding percentages of non-recyclable material discussed herein. It is worth noting though, that the barrier material may be recyclable via other recycling means, e.g. plastic film, plastic bag recycling.

There is currently no universal standard for determining whether a natural material is recyclable. In general, the higher the content of natural material, e.g. natural fibers, and the lower the content of non-recyclable material, the higher the likelihood of being recyclable. Some specific examples of standards which may be useful in determining whether package material is recyclable include the PTS method and Western Michigan method, and each is described below in additional detail. These methods pertain to the recyclability of materials which comprise wood fibers and/or pulp fibers.

Package materials of the present disclosure may comprise natural fibers, e.g. wood fibers and/or pulp fibers) which form a paper. The package material may comprise at least 50 percent by weight natural fibers, at least 70 percent by weight natural fibers, or at least 90 percent by weight natural fibers, specifically reciting all values within these ranges and any ranges created thereby. As yet another example, the package material may comprise 99.9 percent by weight natural fibers. The package materials of the present disclosure may comprise between 50 percent by weight to 100 percent by weight natural fibers, between 70 percent by weight to 99.9 percent by weight, or between 90 percent by weight to 99.9 percent by weight natural fibers. It is worth noting that where the weight percentage of natural fibers is less than 100 percent, the remaining weight percentage may be occupied by coatings, colorants, adhesives and/or other materials, e.g. barrier materials, if desired.

In order to increase the likelihood that the package material is recyclable, the total weight percentage of non-recyclable material, e.g. adhesives, films, coatings and/or colorants, in the package material of the present disclosure may be carefully selected. For example, the package material of the present disclosure may comprise 50 percent by weight or less, 30 percent by weight or less, or about 15 percent by weight or less of non-recyclable material, specifically including all values within these ranges and any ranges created thereby. As another example, the package materials of the present disclosure may comprise from between about 0.1 percent to about 50 percent by weight, from about 0.1 percent to about 30 percent by weight, or from about 0.1 percent to about 15 percent by weight of non-recyclable material, specifically including all values within these ranges and any ranges created thereby. If increased likelihood of recyclability is desired, the weight percentage of non-recyclable materials can be 5 percent by weight or less, or between 0.1 percent to 5 percent by weight, specifically reciting all values within these ranges and any ranges created thereby.

The effectiveness of the recycling process on the package material of the present disclosure may be determined via recyclable percentage. Package material of the present disclosure can exhibit recyclable percentages of 70 percent or greater, 80 percent or greater, or 90 percent or greater, specifically reciting all values within these ranges and any ranges created thereby. The packaging material of the present disclosure can have a recyclable percentage of between 70 percent to about 99.9 percent, from about 80 percent to about 99.9 percent, or from about 90 percent to about 99.9 percent, specifically reciting all values within these ranges and any ranges created thereby. In one specific example, the package material of the present disclosure may exhibit a recyclable percentage of from about 95 percent to about 99.9 percent, from about 97 percent to about 99.9 percent, or from about 98 percent to about 99.9 percent, specifically including all values within these ranges and any ranges created thereby. The recyclable percentage of the package material of the present disclosure can be determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage can be determined via the PTS-RH:021/97 (Draft October 2019) under category II test method. However, unlike the recyclable percentage, in order to increase the likelihood of recyclability, the total reject percentage can be decreased. For example, the total reject percentage of the package material of the present disclosure can be 30 percent or less, about 20 percent or less, or less than about 10 percent or less, specifically including all values within these ranges and any ranges created thereby. For example, the total rejection percentage of the package material of the present disclosure can be from 0.1 percent to 30 percent, from 0.1 percent to 20 percent, or from 0.1 percent to 10 percent, specifically reciting all values within these ranges and any ranges created thereby. In one specific example, the total reject percentage can be less than 5 percent, or between 0.1 percent to 5 percent, 0.1 to 3 percent, or 0.1 to 2 percent, specifically including all values within these ranges and any ranges created thereby.

For the sake of clarity, the percent non-recyclable material does not necessarily have a 1:1 correlation to the total reject percentage. For example, the use of dissolvable adhesives is disclosed herein. As these adhesives are designed to dissolve during the recycling process, it is theorized that these adhesive would not have an impact on the total reject percentage; however, they would contribute to the non-recyclable material weight percent.

It is worth noting that the test method PTS-RH:021/97 (Draft October 2019) under category II, comprises a handsheet inspection component. Trained screeners inspect one or more handsheets of recycled package material for visual imperfections and tackiness. If the number of visual imperfections is too great or if too tacky, then the package material is rejected. If the number of visual imperfections is acceptable and the handsheet is not too tacky, in accordance with the PTS-RH:021/97 (Draft October 2019) method, then the package material is approved for additional processing. The package material of the present disclosure can yield an acceptable level of visual imperfections and tackiness during this step of the PTS method.

The package material of the present disclosure can yield the recyclable percentages mentioned heretofore as well as pass the handsheet screening method. So the package material of the present disclosure can achieve an overall score or final outcome of "pass" when subjected to the PTS-RH:021/97 (Draft October 2019) under category II, recycling test method.

It is also worth noting that there is an alternative method for determining the recyclable percentage of the package material of the present disclosure. The test method performed by the University of Western Michigan called the Repulpability Test can provide a percent yield of recyclable material. The package material of the present disclosure can achieve a percentage yield, in accordance with the Repulpability Test, which is greater than about 70 percent, greater than about 80 percent, or greater than about 90 percent, specifically reciting all values within these ranges and any ranges created thereby. The packaging material of the present disclosure can have a percent yield of between 70 percent to about 99.9 percent, from about 80 percent to about 99.9 percent, or from about 90 percent to about 99.9 percent, specifically reciting all values within these ranges and any ranges created thereby. In one specific example, the package material of the present disclosure can exhibit a percentage yield of recyclable material which is between 80 percent and 99.9 percent, specifically including all values within this range and any ranges created thereby. In such example, the package material may comprise a base color of brown. In another specific example, the package material of the present disclosure can exhibit a percentage yield of recyclable material which is between 85 percent and 99.9 percent, specifically including all values within this range and any ranges created thereby. In such example, the package material may comprise a base color of white. Base colors of package materials are discussed in additional detail herein.

It is contemplated that the package material of the present disclosure, while being recyclable, may itself comprise recycled material. Such determination can be made from a visual inspection of the package material. For example, manufacturers typically advertise the use of recycled materials in an effort to demonstrate their eco-friendly packaging approach. To further expand on this example, some manufacturers may utilize a logo, e.g. a leaf, along with wording to indicate packaging which comprises recycled material. Often times, manufacturers may specify the percentage of recycled material utilized as well, e.g. over 50 percent, over 70 percent, etc.

Visual inspection can be as simple as utilizing the human eye to inspect packages for logos of the use of recycled material. Additionally or alternatively, visual inspection may include microscopy methods such as optical microscopy, scanning electron microscopy or other suitable methods known in the art. For example, package material comprising recycled paper fibers could look different under a microscope due to the presence of a much wider range of natural fiber types than if the package material comprised 100% non-recycled paper. As another example, under a microscope, potentially scanning electron microscope, recycled fibers, due to their processing may appear more fibrillated than their virgin fiber counterparts.

Package Seals

As noted previously, packages of the present disclosure may also comprise a plurality of seals. Seals are package material seams which have been attached. Seams are areas of the package where at least two portions of the package material have the ability to overlap one another. Seals are created when the at least two portions of the package material in the seam are joined to one another, e.g. via adhesive. For example, a bottom panel may comprise seams where ends of the package material overlap. An adhesive may be provided on an interior surface of a first portion of the bottom panel and/or on an exterior surface of a second portion of the bottom panel as well as on an exterior surface of a base portion of the bottom panel to create one or more seals. The top panel may comprise seals where ends of the package material are joined together similar to the seals of the bottom panel. While the seals may be provided on any panel of the package, it is recommended that a consumer-facing panel not include seams or seals. Seams and seals can be visibly non-appealing for consumers.

It is worth noting that seams may comprise overlap areas of package material as described heretofore. Namely, adhesive may be applied on an inner surface of a first portion of the package material and/or an outer surface of a second portion of the package material. The first portion and the second portion can then be joined together to create an overlap seal. However, butt seals may also be created. Butt seals can be created where adhesive is applied to the inner surface of a first portion of the package material and/or the inner surface of a second portion of the package material. The inner surfaces of the first portion and the second portion may be joined to form a butt seal. Butt seals and overlap seals are discussed in additional detail hereafter.

The seals are important to ensure that the packages of the present disclosure reduce the likelihood of exposing the one or more absorbent articles therein to the environment outside of the package material. The use of seals, as described herein, can provide adequate sealing of the package material such that absorbent articles within the package are not exposed to the exterior environment. Simply folding or rolling of the package material does not form a seal as described herein.

In order to survive the rigors of the shipping, stocking, and handling by the consumer, the seals should have a requisite strength. Complicating the requirement for the requisite seal strength are a few variables, i.e. the type of seal and the level of compression of the one or more absorbent articles within the package. An additional complication is that adhesives are considered non-recyclable material. However, the inventors have surprisingly found that with careful selection of the type of adhesive and/or other sealing mechanism, e.g. polyethylene film, as well as the weight percentage, the seal strength requirements can be met along with maintaining the recyclability of the package material.

Regarding the types of seals, the plurality of seals of the packages of the present disclosure may comprise an access seal, a hoop seal, and a bottom seal. Flow wrap packages may be configured to comprise these seals as well. Or, the flow wrap packages may comprise a pair of opposing end seals and a hoop seal between the end seals. In this configuration, an access seal may similarly be provided.

The access seal may be provided as a seal which is opened by the consumer to access the one or more absorbent articles within the package. The hoop seal can be the initial seal created in the package making process. The hoop seal is described in additional detail regarding FIGS. 1A and 1B. An additional variant of the hoop seal, namely where the hoop seal comprises one or more side seals is described regarding FIGS. 4A and 4B. The bottom seal can be located on the bottom panel. The bottom seal and its configuration are discussed in additional detail hereafter regarding FIGS. 2A-2D. The end seals are also discussed hereafter regarding FIGS. 3A and 3B.

In general the packages of the present disclosure may comprise seals which have a tensile strength of at least 3 N/in. For example, each of the plurality of seals of the packages of the present disclosure may have a tensile strength of between 3N/in to about 40 N/in, from about 3N/in to about 35 N/in, or from about 3N/in to about 30 N/in, specifically reciting all values included within these ranges and any ranges created thereby. For packages comprising absorbent articles which do not comprise a large amount of compression, e.g. menstrual pads, light adult incontinence pads, liners, packages with 6 or less absorbent articles therein, and the like, the tensile strength of the seals of this package may be from about 3 N/in to about 25 N/in, from about 3 N/in to about 20 N/in, or from about 3 N/in to about 15 N/in, specifically reciting all values within these ranges and any ranges created thereby.

For packages comprising compressed absorbent articles, the hoop seal may comprise a higher tensile strength than at least one of the other seals. For example, the hoop seal may comprise a tensile strength of between 15N/in to about 40 N/in, from about 20 N/in to about 35 N/in or from about 22 N/in to about 30 N/in, specifically reciting all values within these ranges and any ranges created thereby. In such packages, the one or more absorbent articles may comprise diapers or adult incontinence pants or moderate to heavy use adult incontinence pads. Additional examples are contemplated wherein at least one seal comprises a higher tensile strength than another seal. For example, the bottom seal may comprise a higher tensile strength than the hoop seal and/or the access seal. In another example, the access seal may comprise a high tensile strength than the hoop seal, bottom seal, or end seals. In yet another example, at least one end seal may comprise a higher tensile strength than the other end seal and/or the hoop seal.

Additionally, the inventors have surprisingly found that the access seal, can have a lower tensile strength than the hoop seal, and/or any other seal. In forms where the access seal is located on the top panel of the package, there is generally not as much load as on the hoop seal and other seal(s), e.g. bottom seal, end seal. It is worth noting that the access seal may be disposed on one or more of the top panel, right panel, and/or left panel. Or for flow wrap packages which comprise end seals and a hoop seal, one of the end seals can act as the access seal.

Alternatively, packages of the present disclosure may be configured such that the seals comprise similar tensile strengths. For example, each of the plurality of seals can have a tensile strength of at least 10N/in. In such forms, each of the seals can have a tensile strength which is within 15% of the tensile strength of the remainder of the seals of the package. However, as noted previously, since adhesives and/or other sealing mechanisms, e.g. polyethylene film, are considered non-recyclable material, their use should be carefully reviewed to ensure that the package material maintains its ability to be recycled. The tensile strengths of the seals mentioned herein can be determined by the tensile test method described in ASTM F88-06 as modified herein.

As was noted previously, the type as well as amount of adhesive utilized for the seals of the packages of the present disclosure can impact the recyclability of the package. As an example, adhesives which can dissolve in water during the re-pulping stage of the disintegration step of the recycling process may be particularly suitable for the packages of the present disclosure. Such adhesives include starch based adhesives, polyvinyl alcohol based adhesives, and polyethylene oxide based adhesives. One suitable example of a starch based adhesive is available from LD Davis located in Monroe, North Carolina, under the trade name AP0420CR. One suitable example, of a polyvinyl alcohol based adhesive is available from Sekisui Chemical Company, located in Osaka, Japan, under the trade name Selvol 205. One suitable example of a polyethylene oxide based adhesive is available from Dow Chemicals Co. located in Midland, Michigan, under the trade name WSR N-80.

If the adhesive is not water-soluble, then water-dispersible adhesives may similarly be utilized. Suitable examples of water dispersible adhesives include thermoplastic elastomer based adhesives and polyvinyl acetate based adhesives. One suitable example of a thermoplastic elastomer based adhesive is available from Actega located in Blue Ash, Ohio, under the trade name Yunico 491. One suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Any suitable pressure sensitive adhesives may be utilized as well. One suitable example of a pressure sensitive adhesives includes sold by Formulated Polymer Products Ltd. Located in Bury, Lancashire, England, and sold under the trade name FP2154. As one specific example, the access seal may comprise a pressure sensitive adhesive.

Without wishing to be bound by theory, it is believed that packages of the present disclosure which utilize adhesives dissolvable in water may comprise a higher weight percentage of such adhesives than adhesives which are only water dispersible. For example, packages comprising water dissolvable adhesives may comprise a first weight percentage of adhesive while packages comprising water dispersible adhesives may comprise a second weight percentage of adhesive. It is believed that the first weight percentage may be greater than the second weight percentage for the purposes of recycling the package material. Data regarding suitable weight percentages of adhesive are provided below in Table 1.

The following Samples are shown in Table 1. Samples 1 through 4: Available from BillerudKorsnäs™ under the trade name Axello Zap.

TABLE 1

| Sample No. | Paper basis weight (gsm) | Type of Adhesive | Weight percentage of paper (%) | Weight percentage of adhesive (%) |
|---|---|---|---|---|
| Sample 1 | 80 | Thermoplastic elastomer | 98 | 2 |
| Sample 2 | 80 | Polyvinyl acetate strips | 97 | 3 |
| Sample 3 | 80 | Polyvinyl acetate | 86 | 14 |
| Sample 4 | 80 | Starch | 86 | 14 |

Table 2 below shows the recyclability data based upon the PTS method and the Western Michigan test mentioned previously. It is believed that the recyclable percentages achieved via the PTS method would be similar to the percent yield of recyclable material determined by the Western Michigan test for Samples 1 and 2 which were only tested under the PTS method.

TABLE 2

| Sample No. | Western Mich. percent fiber yield (%) | PTS recyclable percent (%) | PTS Handsheet inspection | PTS Score |
|---|---|---|---|---|
| Sample 1 | N/A | 99 | Pass | Pass |
| Sample 2 | N/A | 99.1 | Pass | Pass |
| Sample 3 | 99.2 | 99.8 | Fail | Fail |
| Sample 4 | 100 | 100 | Pass | Pass |

As noted previously, the packages of the present disclosure may utilize a dissolvable adhesive, dispersible adhesive, pressure sensitive adhesive, or any combination thereof. However, the choice of adhesives should be considered carefully from a weight percentage standpoint. Where dissolvable adhesives are utilized, the adhesive may comprise at least one of the following: starch based, polyethylene oxide based, polyvinyl alcohol based, or combinations thereof. Sample 4 illustrates that even at 14 percent by weight, the dissolvable adhesive (starch based) passed the PTS method disclosed herein whereas polyvinyl acetate at the same weight percentage did not pass the PTS test.

Where dispersible adhesives are desired, much like the foregoing, care should be taken to ensure that the packaging material maintains its ability to be recycled. Where an adhesive, such as a polyvinyl acetate based adhesive is desired, the weight percentage can be about 12 percent by weight or less, about 10 percent by weight or less, specifically reciting all values within these ranges and any ranges created thereby. For example, polyvinyl acetate based adhesives can be utilized in an amount of from between about 0.5 percent by weight to about 12 percent by weight, from about 0.5 percent by weight to about 10 percent by weight, or 0.5 percent by weight to about 7 percent by weight, specifically reciting all values within these ranges and any ranges created thereby.

The foregoing weight percentages are believed to be applicable to achieve a total reject percentage of less than 5 percent in accordance with the PTS method mentioned herein as well as pass the handsheet inspection. As the data demonstrates, while 14 percent by weight of polyvinyl acetate failed the PTS method, it passed the Western Michigan method. It is believed that higher weight percentages of polyvinyl acetate may be utilized in some package materials of the present disclosure and still meet the recyclability requirements of some jurisdictions, e.g. Western Michigan. For example, the weight percentage of polyvinyl acetate adhesives for the Western Michigan test are believed to be in the ranges of 0.5 to about 20 percent by weight, 0.5 to about 15 percent by weight, or from about 0.5 to about 10 percent by weight, specifically reciting all values within these ranges and any ranges created thereby.

However, it is worth noting that where the dispersible adhesive is a thermoplastic elastomer based adhesive, different weight percentages may apply. For example, where the dispersible adhesive comprises a thermoplastic elastomer based adhesive, the weight percentage may be about 7 percent by weight or less, about 5 percent by weight or less, or about 4 percent by weight or less, specifically reciting all values within these ranges and any ranges created thereby. Further in this example, the weight percentage may be from between about 0.5 percent by weight to about 7 percent by weight, from about 0.5 percent by weight to about 5 percent by weight, or from about 0.5 percent by weight to about 4 percent by weight, specifically reciting all values within these ranges and any ranges created thereby.

Similar to the polyvinyl acetate adhesive, the foregoing weight percentages are believed to be applicable to achieve a total reject percentage of less than 5 percent as well as the handsheet inspection in accordance with the PTS method mentioned herein. It is believed that higher weight percentages of thermoplastic elastomer based adhesive may be utilized while still meeting the recyclability requirements of some jurisdictions, e.g. Western Michigan. For example, the weight percentage of thermoplastic elastomer based adhesives for the Western Michigan test are believed to be in the ranges of 0.5 to about 15 percent by weight, 0.5 to about 12 percent by weight, or from about 0.5 to about 7 percent by weight, specifically reciting all values within these ranges and any ranges created thereby.

The inventors have surprisingly found dispersible adhesives, such as thermoplastic elastomer and polyvinyl acetate based adhesives, can provide great seal strength while also being extremely flexible from an application standpoint. For example, where heat sealing is already utilized as part of an existing manufacturing line, these adhesives allow for the same flexibility, namely being heat sealable. As another example, these adhesives could be printed onto the packaging material which facilitates manufacturing. As another example, these adhesives can be applied via pattern coat or partial coat. Building on this example, these adhesives allow for the seal strength to be manipulated to a desired outcome. These adhesives may be applied in patterns, e.g. stripes, dots, etc. In this manner, these adhesives can provide the desired amount of seal strength in the desired location. Because of the flexibility in application of these adhesives to the package material of the present disclosure, seal strengths can be adjusted easily.

Regarding adhesive application, the inventors have surprisingly found that patterned application of adhesive can provide higher seal strength than full coat, i.e. solid coat, of adhesive. While solid coating of adhesive can still be utilized to achieve the seal strength values described herein, striped patterns may provide the same level of tensile strength while having the added advantage of using less adhesive. As an example, the inventors surprisingly found that adhesive applied in horizontal stripes (parallel or perpendicular to the longest dimension of the seal) as well as angled and cross hatch patterns, provided seal strengths similar to full coat applications while using less adhesive. So, packages of the present disclosure that comprise a discontinuous application of adhesive in at least one seal are contemplated.

It is worth noting that the characteristics of the seals of the packages of the present disclosure may depend on how the package material is processed. For example, an absorbent article manufacturer may purchase the package pre-formed. In such instances, the absorbent article manufacturer may receive from a paper package manufacturer essentially an open bag comprising a panel with a hoop seal and a panel with another seal, e.g. bottom seal. The other seal, e.g. bottom seal, may be configured in a block style, a cross style or pinch style arrangement. Such configurations are discussed in additional detail hereafter regarding FIGS. 2A-2D.

In creating an access seal, the absorbent article manufacturer may utilize the same adhesive utilized in the hoop seal and/or other seal, e.g. bottom seal. Alternatively, the absorbent article manufacturer may utilize an adhesive which is different than that of the hoop seal and/or the other seal, e.g. bottom seal.

It is also possible that the absorbent article manufacturer produces the packages themselves. For example, an absorbent article manufacturer may have the capability to produce the open bag, similar to above and subsequently fill it with one or more absorbent articles and thereafter seal it without the need for purchasing such bags from a supplier.

Another example where an absorbent article manufacturer produces the packages themselves include the flow wrap configuration. In such configuration, the manufacturer forms the package about the one or more absorbent articles as opposed to placing the one or more absorbent articles into a pre-formed bag. These types of packages of the present disclosure may comprise end seals and a hoop seal and may additionally comprise an access seal or one of the end seals may comprise the access seal.

Regardless of whether an absorbent article manufacturer purchases pre-made bags from a supplier or make the packages themselves, the foregoing seal configurations may still be provided. Namely, at least one seal may comprise a different adhesive than the other seals, or the adhesive in the seals may comprise the same adhesive.

Some contemplated examples include packages where the hoop seal and other seal, e.g. bottom seal, end seal(s), comprise a dissolvable adhesive and wherein the access seal or end seal comprises a dispersible adhesive. Another contemplated example is where the hoop seal and other seal, e.g. bottom seal, end seal(s), comprise a dissolvable adhesive and where the access seal or end seal comprises a pressure sensitive adhesive. Another contemplated example is where all of the seals comprise dispersible adhesives. Another example is where all of the seals comprise dissolvable adhesives. Still another example is where all of the seals comprise the same adhesive, e.g. a pressure sensitive adhesive, a dissolvable adhesive, or a dispersible adhesive. Still another example is where at least one of the plurality of seals comprises a pressure sensitive adhesive.

Coatings and Colorants

Each of the plurality of panels comprises an inner surface and an outer surface. The outer surface and/or inner surface of one or more panels may comprise colorants and/or coatings, which create branding on the package, package information, and/or background color, etc. The branding and/or package information can be provided on an outer surface and/or inner surface of at least one panel, e.g. the consumer-facing panel. Branding can include logos, trade names, trademarks, icons, and the like, associated with the absorbent articles within the package. Branding can be utilized to inform a consumer of the brand of the absorbent articles within the package. As an example, branding for a package of feminine hygiene pads may comprise the brand name Always®.

Package information can include the size of the absorbent articles, the number of absorbent articles within the package, an exemplary image of the absorbent articles contained within the package, recyclability logos, and the like, associated with the absorbent articles within the package. Additionally, package information can include information regarding the package material itself, e.g. recyclability logos, certifications from various organizations, or the like. As an example, package information for a package of feminine hygiene pads may comprise a size indicator, e.g. "Size 1." Other panels of the package may similarly include branding, package information, and/or background color, along with that associated with the consumer-facing panel.

Additionally, one or more panels of the packages of the present disclosure may comprise colorants and/or coatings, to provide a background color to the packages of the present disclosure. To further clarify the background color, it is worth noting that the packaging material comprises a base color. A base color of the package material is the color of the package material without colorants and/or coatings. For example, bleached package material is white in color, unbleached is brown in color, and package material which includes recycled content can be grey in color. A background color is any color that is not a base color, e.g. blue, red, green, yellow, purple, orange, black, or combinations thereof. However, background color can also include white, brown, or grey, if the background color is achieved via colorants and/or coatings.

As noted previously, the use of colorants and/or coatings may be considered to be contaminants in the recyclability stream. So the use of colorants and/or coatings should be carefully reviewed.

In order to reduce the use of colorants and/or coatings, for the benefit of the recycling process, a base color of the package material may be utilized. For example, packages where the consumer-facing panel comprises branding, package information, and/or background color, while one or more panels comprise a base color are contemplated. In one specific example, the bottom panel and/or back panel may utilize the base color of the package material instead of a background color. One or more of the bottom panel, top panel, left panel, right panel, back panel, or any combination thereof may utilize the package material base color instead of a background color. In another example, the consumer-facing panel independently or in conjunction with other panels may comprise a base color. To further build on this example, the package may comprise absorbent articles which comprise natural-based components, e.g. cotton topsheet and/or non-chlorine bleached pulp in an absorbent core. In such examples, the consumer-facing panel may comprise a base color of white. In this same example, in conjunction with the base color, the consumer-facing panel may further comprise branding, background color (associated with the branding), and/or package information. In still another example, one or more panels may comprise package information, which in part, comprises a base color. To further build on this example, the base color may be a first color, e.g. white, and a background color may be applied to a panel with a negative image of the package information, such that the package information, or a portion thereof, is not covered by the background color, and the package information comprises the base color.

Still in other examples, the seams of the packages of the present disclosure may comprise less colorant coverage than adjacent areas on the same panel. For example, a portion of a panel which is joined to another portion of the panel to form a seal, may comprise a seam area. The seam area may comprise less colorant or even no colorant than the portion of the panel adjacent thereto. Each seal may comprise a seam area which comprises less colorant or even no colorant than an adjacent area to the seal.

Still in other examples, a first panel may comprise a colorant percent coverage which is different than a second panel. Further elucidating this example, the consumer-facing panel may have a colorant percent coverage which is higher than another panel of the package, e.g. bottom panel. As noted, absorbent articles which are natural based, e.g. cotton topsheets or other components, non-chlorine bleached cores, no added colorants, and/or no added scents, may rely more on the base colors of the package material. As an example, such packages may comprise a consumer-facing panel comprising a colorant coverage of 75 percent or less, 50 percent or less, or 40 percent or less. Further the consumer-facing panel may comprise a colorant coverage of from between about 10 percent to about 75 percent, from about 15 percent to about 50 percent, or from about 20 percent to about 40 percent, specifically reciting all values within these ranges and any ranges created thereby.

In such packages other panels may be configured having a higher percentage of colorant coverage, lower percentage, or a mix thereof. For example, in such configurations, a bottom panel may comprise a lower percentage of colorant coverage. A back panel, left panel, and/or right panel may comprise a higher percent colorant coverage percentage or a lower percentage of colorant coverage. These same values may apply for flow wrap configurations described herein as well. Colorant coverage percentage is determined via the Percentage of Colorant Coverage Measurement Method described herein Natural based products as described are not necessarily limited to the foregoing colorant coverages; however, less colorant percentage can mean less colorant weight percentage which can be beneficial from a recyclability standpoint. In another example, absorbent article packaging in accordance with the present disclosure may comprise a consumer-facing panel having a colorant coverage of 100 percent, 99 percent or less, or 98 percent or less. For example, packages in accordance with the present disclosure may comprise a consumer-facing panel having a colorant coverage percentage of from between 60 percent to about 100 percent, from about 60 percent to about 99 percent, or from about 60 percent to about 98 percent. In such configurations, other panels may comprise the same percentage of colorant coverage or may comprise a lower percent of colorant coverage. Colorant coverage percentage is determined via the Percentage of Colorant Coverage Measurement Method described herein.

While any suitable colorants may be utilized, the inventors have surprisingly found that water based colorants typically dissolve more readily in water during the recycling process. So, water based colorants can facilitate the recycling process for the packages of the present disclosure. Any suitable water based colorant may be utilized. Water based colorants are well known in the art.

It is worth noting that solvent based colorants and/or energy curable colorants may also be utilized. However, the use of these types of colorants can add complication to the manufacturing of the package material. For example, solvent based colorants generally exhaust volatile organic compounds which are required to be removed from the air. Additionally, solvent based colorants may comprise components which do not readily dissolve in water during the recycling process which could negatively impact the recyclability of the package material.

Energy curable colorants may also be utilized; however, much like the solvent based colorants, energy curable colorants can add complication to the processing of the package material. And much like the solvent based colorants, the energy curable colorants may comprise components which are not readily dissolvable in water during the recycling process which could negatively impact the recyclability of the package material.

Any suitable coating utilized for packaging material may be utilized. Coatings can be utilized to protect the background color, branding, and/or package information. Additionally, coatings may be utilized to provide anti-static benefits, coefficient of friction benefits, and/or appearance benefits, e.g. gloss, matte, satin, high gloss, etc.) Much like water based colorants, the inventors have surprisingly found that water based coatings, if utilized, may facilitate the recycling process of the package material. Suitable coatings comprise varnishes which are well known in the art. Any suitable coating/varnish may be utilized.

In order to withstand the rigors of a manufacturing process where a plurality of absorbent articles is disposed within the package, withstand the rigors of being shipped, provide protection from environmental insults during shipping and while on the store shelf, and provide for product protection while in the consumers home, the package material may have some level of strength, stretch, and resilience. As an example, package material of the present disclosure may exhibit an MD tensile strength of at least 4.7 kN/m, at least 7 kN/m, or at least 8 kN/m, specifically reciting all values within these ranges and any ranges created thereby. The MD tensile strength may be between 4.7 kN/m to 8.5 kN/m, or between 5.2 kN/m and 8.2 kN/m, or between 5.5 kN/m and 8.0 kN/m, specifically reciting all values within these ranges and any ranges created thereby. The MD tensile strength is measured using ISO 1924-3 as modified herein.

As another example, the package material of the present disclosure can exhibit a CD tensile strength of at least 2.7 kN/m, at least 4 kN/m, or at least 5.5 kN/m, specifically reciting all values within these ranges and any ranges created thereby. The CD tensile strength may be between 2.7 to 6.5 kN/m, between 2.7 to 6.2 kN/m, or between 2.7 to 6 kN/m, specifically reciting all values within these ranges and any ranges created thereby. The CD tensile strength is measured using ISO 1924-3 as modified herein.

As another example, the package material of the present disclosure can exhibit a burst strength of at least 185 kPa, at least 250 kPa, or at least 550 kPa, specifically reciting all values within these ranges and any ranges created thereby. The burst strength of the package material of the present disclosure can be between 185 to 600 kPa, between 220 to 550 kPa, or between 250 to 500 kPa, specifically reciting all values within these ranges and any ranges created thereby. The burst strength is measured using ISO 2758 as modified herein.

As another example, the package material of the present disclosure may exhibit an MD stretch at break, at least 3 percent, or at least 6 percent, specifically reciting all values within these ranges and any ranges created thereby. The package material of the present disclosure can exhibit an MD stretch at break of between 3 to 6.5 percent, between 3.2 to 6.2 percent, or between 3.5 to 6 percent, specifically reciting all values within these ranges and any ranges created thereby. The MD stretch at break is measured using ISO 1924-3 as modified herein.

As another example, the package material of the present disclosure can exhibit a CD stretch at break of at least 4 percent, at least 6 percent, or at least 9 percent, specifically reciting all values within these ranges and any ranges created thereby. The package material of the present disclosure can exhibit a CD stretch at break of from 4 to 10 percent, from 4.5 to 9.5 percent, or from 5 to 9 percent, specifically reciting all values within these ranges and any ranges created thereby. The CD stretch at break is measured using ISO 1924-3 as modified herein.

As yet another example, the basis weight of the package material can affect the "feel" of the package to the consumer in addition to affecting the strength and resilience of the package material. Too low of a basis weight and the package can feel too flimsy. Too high and the package can feel too inflexible. The package material of the present disclosure can have a basis weight of between 50 to 120 gsm, between 60 to 105 gsm, or between 70 to 90 gsm, specifically reciting all values within these ranges and any ranges created thereby. The basis weight can be determined via ISO 536 as modified herein.

It is worth noting that the lower basis weight of 50 gsm may require some precautions during processing. For high speed packaging processes, a basis weight of 50 gsm may not provide the desired level of reliability. It is believed that high speed packaging processes may induce strain into the packaging material that slower packaging processes may not. So from a high speed manufacturing standpoint, 60 gsm may be the lowest desirable package material basis weight. Where hand packing or lower speed packaging processes are utilized, 50 gsm may be sufficient as the lowest package material basis weight.

Regarding caliper, the package material of the present disclosure can exhibit caliper of at least 50 μm, at least 70 μm, or at least 90 μm, specifically reciting all values within these ranges and any ranges created thereby. The package material of the present disclosure can exhibit caliper of between 50 to 110 μm, from 55 to 105 μm, or from 60 to 100 μm, specifically reciting all values within these ranges and any ranges created thereby. The caliper is measured using ISO 534 as modified herein.

It is worth noting that the package material of the present disclosure is different than cartonboard, cardboard, and brown paper bags. For example, cartonboard is not as flexible as the package materials of the present disclosure. Cartonboard is designed and is inherently stiffer than the package materials of the present disclosure and can be more difficult to process on converting lines due to their stiffness. Additionally, cartonboard has a higher basis weight than do the package materials of the present disclosure.

Similarly, cardboard is also different than the package materials of the present disclosure. Cardboard has a much higher basis weight than the package materials of the present disclosure. Additionally, cardboard is much less flexible than the package materials of the present disclosure. Cardboard materials are commonly fluted and comprise three plies of a paper material and as such, is structurally different than the package materials of the present disclosure. Additionally, the package material of the present disclosure has a much lower basis weight than does cardboard.

Some advantages that the packaging material of the present disclosure have over cartonboard and cardboard include the flexibility as discussed herein. However, another advantage is that the package materials of the present disclosure take up less space than their more-bulky cartonboard and cardboard counterparts. Another advantage of the package materials of the present disclosure is that they allow the absorbent articles therein to be compressed within the package. This allows for more products to fit within a smaller volume package which also enable efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Regarding brown paper bags which were prevalent in grocery stores for carrying groceries, the packages of the present disclosure are also different. As discussed in additional detail herein, the package material of the present disclosure is sealed such that the absorbent articles are enclosed and protected from the external environment by the package material. More specifically, the package of absorbent articles in accordance with the present disclosure does not have an opening into which items can be placed. Instead, the package of absorbent articles in accordance with the present disclosure is sealed to reduce the likelihood of contamination of the absorbent articles during shipping, stocking, and sitting on store shelves. In contrast, the conventional brown paper bags widely used in grocery stores decades ago, comprise an opening into which items can be placed.

Despite having reduced flexibility compared to plastic packaging and lower basis weight than cardboard and cartonboard, the inventors have surprisingly found the packaging material of the present disclosure can withstand the rigors of a manufacturing process where a plurality of absorbent articles is placed within the package as well as the rigors of being shipped, provide protection from environmental insults during shipping, and while on the store shelf, and provide for product protection while in the consumers home.

It is also worth noting that the package material of the present disclosure, in addition to lacking the high stretch properties of conventional plastic packaging film, may not provide the barrier properties of a conventional plastic packaging film. For example, the package material of the present disclosure may not comprise a functional, barrier layer such as a layer of foil, plastic, or the like. However, as disclosed herein, forms are contemplated where package materials of the present disclosure comprise a film disposed on an inner surface of the packaging material. This film can serve as a barrier to moisture vapor transmission through the packaging material.

In addition, examples are contemplated where the absorbent article backsheet is in direct contact with the inner surface of the package material. Packages of the present disclosure comprising diapers may be configured in this manner Feminine hygiene pads, including menstrual pads, liners, adult incontinence pads, and the like, may be individually wrapped in order to protect panty fastening adhesive on their respective backsheets. In packages with these articles, the individually wrapped article may be in direct contact with the inner surface of the package material. Forms are contemplated where the wrapper which wraps the individual articles may comprise natural fibers as described herein. Additionally, such wrappers may be recyclable as described herein.

Figure 1B:
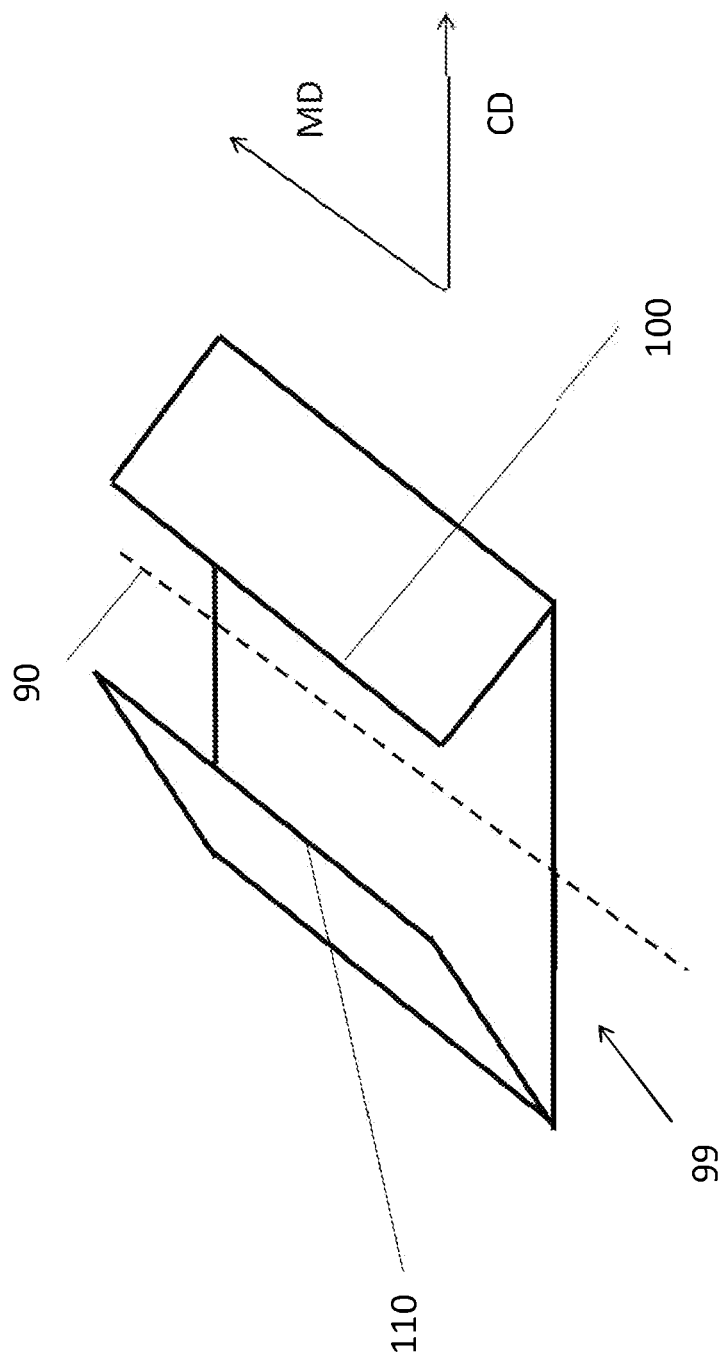
FIG. 1B is a schematic representation showing the package material sheet of FIG. 1A in a folded configuration.

As noted previously, absorbent article manufacturers may purchase the packaging material already preformed into open bags or may purchase rolls of packaging material. Regardless of whether the package material is on rolls or pre-formed to some extent, the packages of the present disclosure begin with paper stock. Referring to FIGS. 1A-1B, edge portions 100 and 110 of a paper stock sheet 99 may be folded in on themselves and subsequently joined together to form a seal. For example, side portions 100 and 110 of the sheet 99 may be folded or simply translated transversely inward towards a longitudinal centerline 90 of the sheet 99. These edge portions can be overlapped with one another and joined together to form an overlap seal. Alternatively, the edge portions 100 and 110 may be joined together on their respective inner surfaces to form a butt seal. It worth noting that butt seals tend to not lay as flat as overlap seals. So where the seal is located, at least in part, on a bottom panel, an overlap seal may be desirable such that the package sits on a more-flat bottom panel. The joining of the edge portions 100 and 110 is referred to as the hoop seal.

Figure 1D:
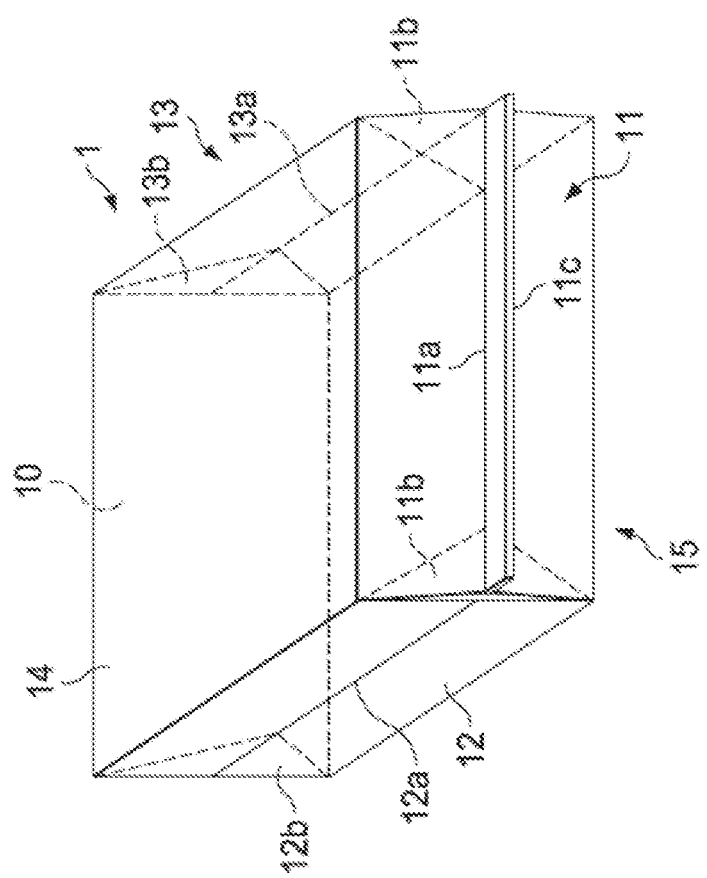
FIG. 1D is a schematic representation of the package of FIG. 1C in a closed state.
Figure 1E:
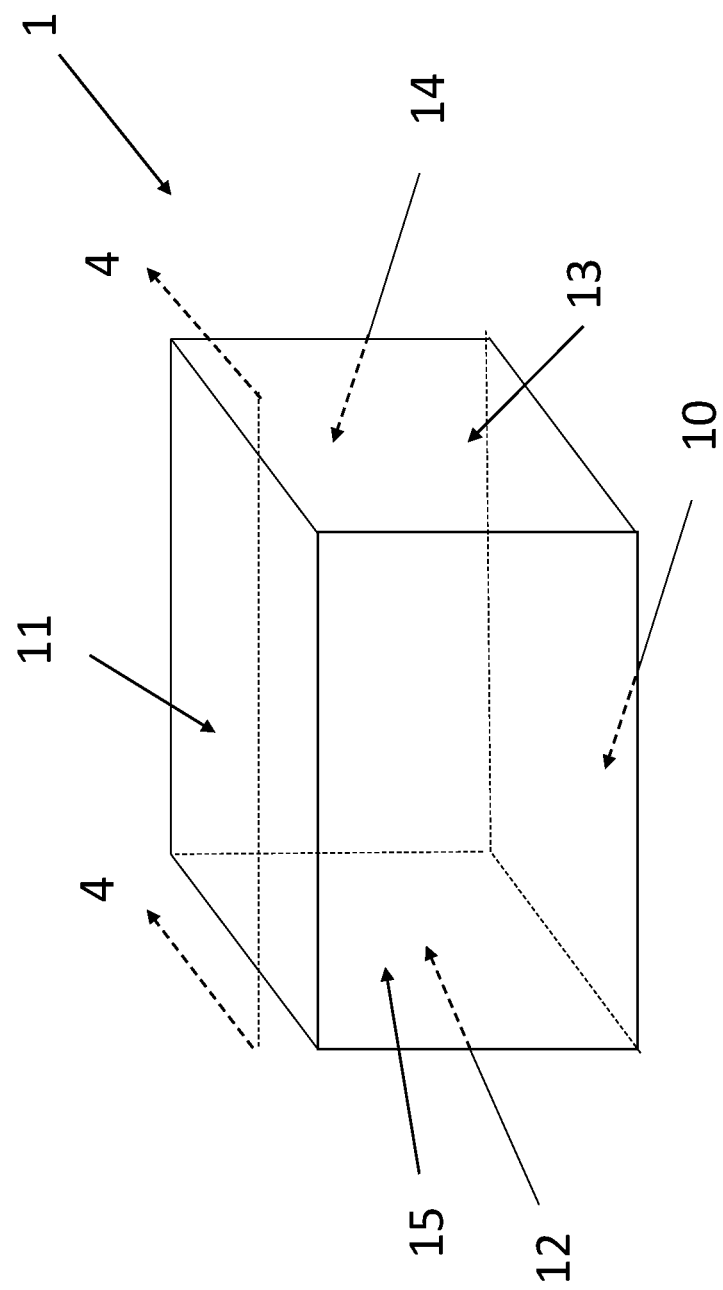
FIG. 1E is a schematic representation of another package of the present disclosure shown in a closed state.

Referring now to FIGS. 1C-1E, the sheet of packaging material may be suitably folded to form bag side creases 12b and 13b and two side folds 12a and 13a on opposite sides, to form the bag structure 4 having a first surface 10, a second and third surface 12, 13, respectively, and a fourth and a fifth surface 14, 15. An open end 48 (e.g., a gusseted bag structure) opposes the first surface 10. Each side crease 12b, 13b is located at the respective second or third surface 12, 13. It is worth noting that in FIGS. 1C and 1D, the crease and folds shown are for a package having a block configuration or block bottom configuration. Gussets and fold lines for a pinch bottom bag are discussed in additional detail regarding FIG. 2B.

The bag 4 may be filled by inserting articles such as a stack of absorbent articles through the open end 48. When the bag 4 is filled with a plurality of articles, e.g. by entering articles from the open end 48, the device used to introduce the articles inside the bag 4 together with the articles may exert some tension on each of the second and third surfaces 12, 13 of the bag 4. For example, the articles can be compressed before being inserted into the bag 4. So the articles may slightly expand after they are introduced in the bag 4 and thus exert some tension on the second and third surfaces 12, 13 as well as the fourth surface 14 and the fifth surface 15. The tension is exerted on each of the creases 12b, 13b at the respective second and third surfaces 12, 13, particularly along the first and second side folds 12a, 13a with which the package may maintain a substantially parallelepiped-shape.

As may be appreciated from FIG. 1D, the open end 48 opposite first surface 10 may then be closed to form the sixth surface 11. Any suitable style of closing may be utilized. As an example, the sixth surface may comprise closing gussets 11b by bringing edges of the bag 4 together and bonding them together to form a closing seam 11a and a closing seam fin 11c extending from the closing seam 11a, and sixth surface 11. In yet another example, the sixth surface may comprise seams which are joined together in a block style configuration or cross style configuration discussed hereafter.

Figure 2A:
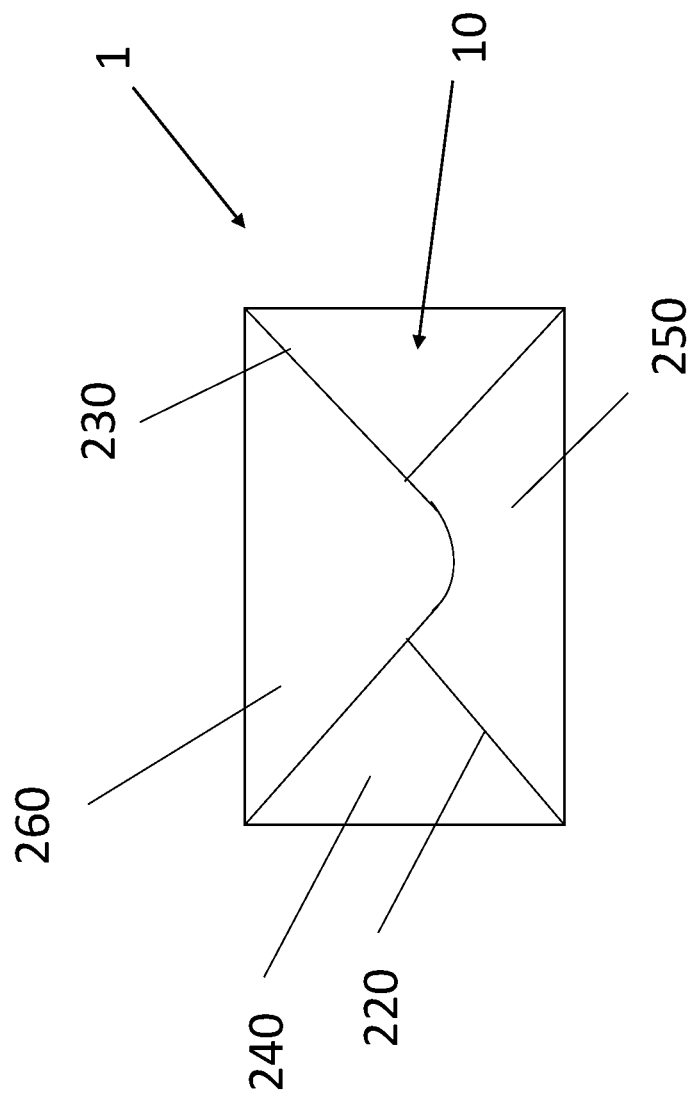
FIG. 2A is a schematic representation showing a panel of a package of the present disclosure, wherein the panel comprises seals in a block style configuration.

An example of a block style configuration is shown in FIG. 2A. As shown, the first surface 10 may comprise a block style configuration comprising seals 220 and 230. The first surface 10 may comprise a base portion 240. A first flap of package material 250 may be folded onto the base portion 240. Adhesive may be provided to attach the first flap of package material 250 to the base portion 240 thereby forming the first seal 220. A second flap of package material 260 may be folded and adhesively attached to the base portion 240 and on top of the first flap of package material 250. Adhesive may be provided to attach the second flap of package material 260 to the base portion 240 and to the first flap of package material 250 thereby forming the second seal 230. A similar execution may be utilized regarding the sixth surface 11. Again for the sake of clarity, adhesive may not be required where a film is provided on an inner surface of the package material.

Figure 2B:
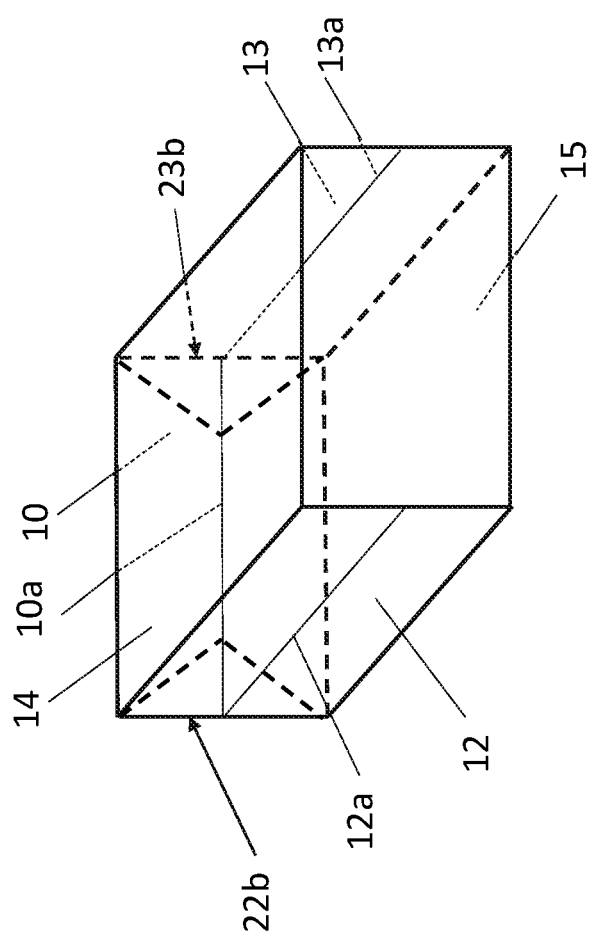
FIG. 2B is a schematic representation showing a package of the present disclosure, wherein the package comprises seals in a pinch bottom configuration.

Another example of a panel sealing style which can be utilized with the packages of the present disclosure is the pinch style configuration or the pinch bottom style. An example of a pinch style configuration is shown in FIG. 2B. As shown, one of the key differences between the block bottom and the pinch bottom configuration is the creases 12b and 13b. Instead of creases on the sides 12 and 13, a pinch style configuration comprises gussets 22b and 23b on the first surface 10. Additionally, in the pinch bottom configuration, the first surface 10 comprises a fold line 10a which may be absent in the block style configuration.

Figure 2C:
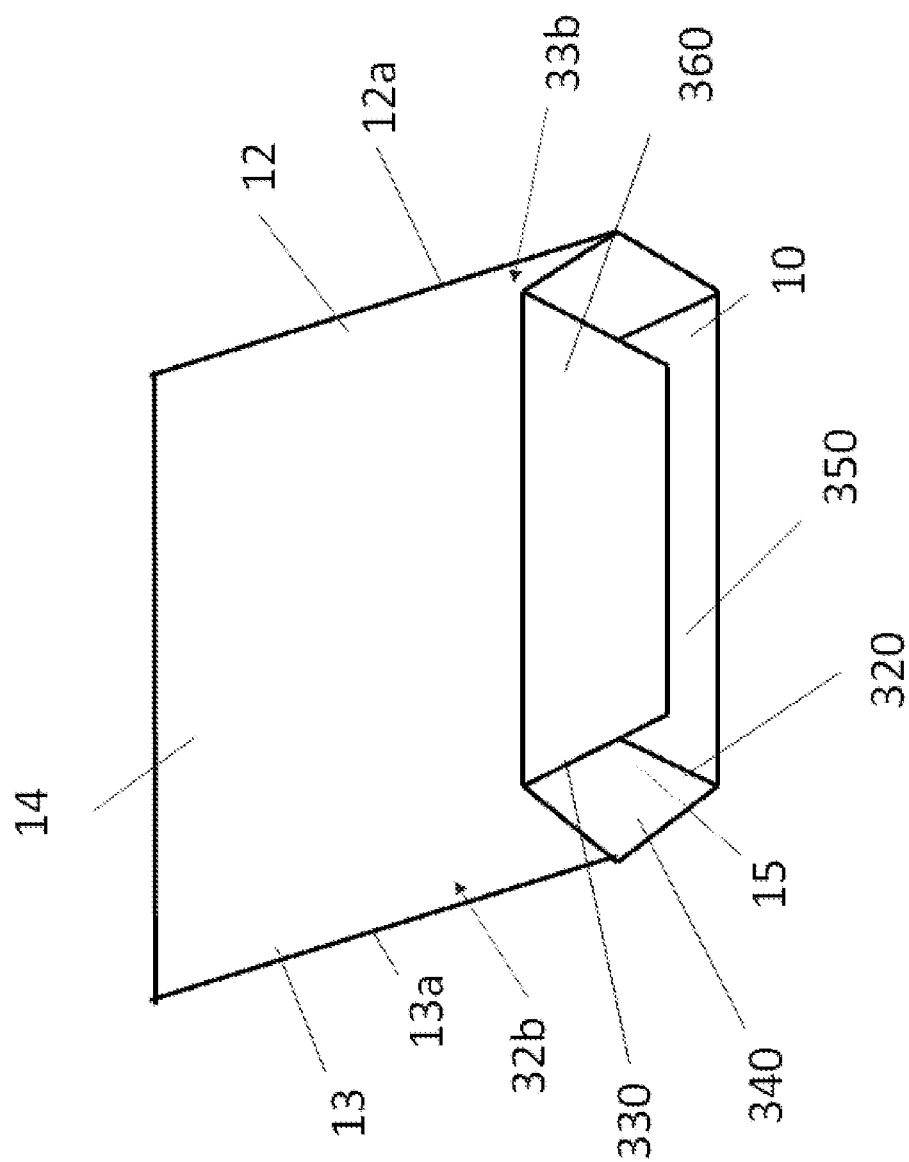
FIG. 2C is a schematic representation showing a package of the present disclosure, wherein the package comprises seals in a cross style configuration.

Cross style configurations are also acceptable for sealing portions of the package material of the present disclosure. An example of a cross bottom style configuration is shown in FIG. 2C. As shown, one of the key differences between the cross style configuration and the block style configuration, is that gussets 32b and 33b are oriented outward. In contrast, fold lines 12a and 13a on the second surface 12 and the third surface 13, respectively in FIG. 1C are oriented inward prior to filling the package. Due to the orientation of the gussets 32b and 33b in the cross style configuration, filling the package with absorbent articles may require less energy to expand the package for filling. As an example, creases oriented inward, e.g. block style configuration, would require displacement outward of the creases prior to filling the package. Additionally, the equipment utilized in guiding the product into the package will have a reduced likelihood of interference with the gussets of the cross bottom configuration given their orientation outward. This can reduce the likelihood of packaging mishaps or manufacturing process stoppages due to quality issues.

Still referring to FIG. 2C, similar to the block style configuration, the first surface 10 of the cross style configuration comprises seals 320 and 330. The first surface comprises a base portion 340. A first flap of package material 350 may be folded and adhesively attached to the base portion 340. First seal 320 may be provided to attach the first flap of package material 350 to the base portion 340. A second flap of package material 360 may be folded onto the base portion 340 and on top of the first flap of package material 350. Second seal 330 may be provided to join the second flap of package material 360 to the base portion 340 and to the first flap of package material 350. A similar execution may be utilized regarding the sixth surface (formed after the placement of absorbent articles therein).

Regardless of the sealing configuration, i.e. block, cross, or pinch, these configurations are known in the art. It is worth noting that for less bulky items where standability of the package is desired, the block bottom or cross bottom, may be desirable. However, for bulky items the pinch style configuration bags may be beneficial as the bulky absorbent articles therein can form a steady base for the package to stand. Additionally, it is worth noting that block style and cross style configuration packages tend to be themselves more-bulky than their pinch style counterparts. For the purposes of packaging, unfilled packages can come in stacks to an absorbent article manufacturer. Typically, stacks of block style and cross style configuration packages will take up more space—due to their bulkiness—than their pinch style counterparts. The bulkiness of the block and cross style configurations can make the stacks more difficult to manipulate during the filling process particularly where a large number of packages are created per minute. In such instances, the bulkiness of these configurations can mean an increased frequency of replenishment of the stacks. So for packages (unfilled) comprising the same packaging material but different sealing style, i.e. block and pinch, the block style configuration will take up more space than their pinch style counterparts.

Figure 2D:
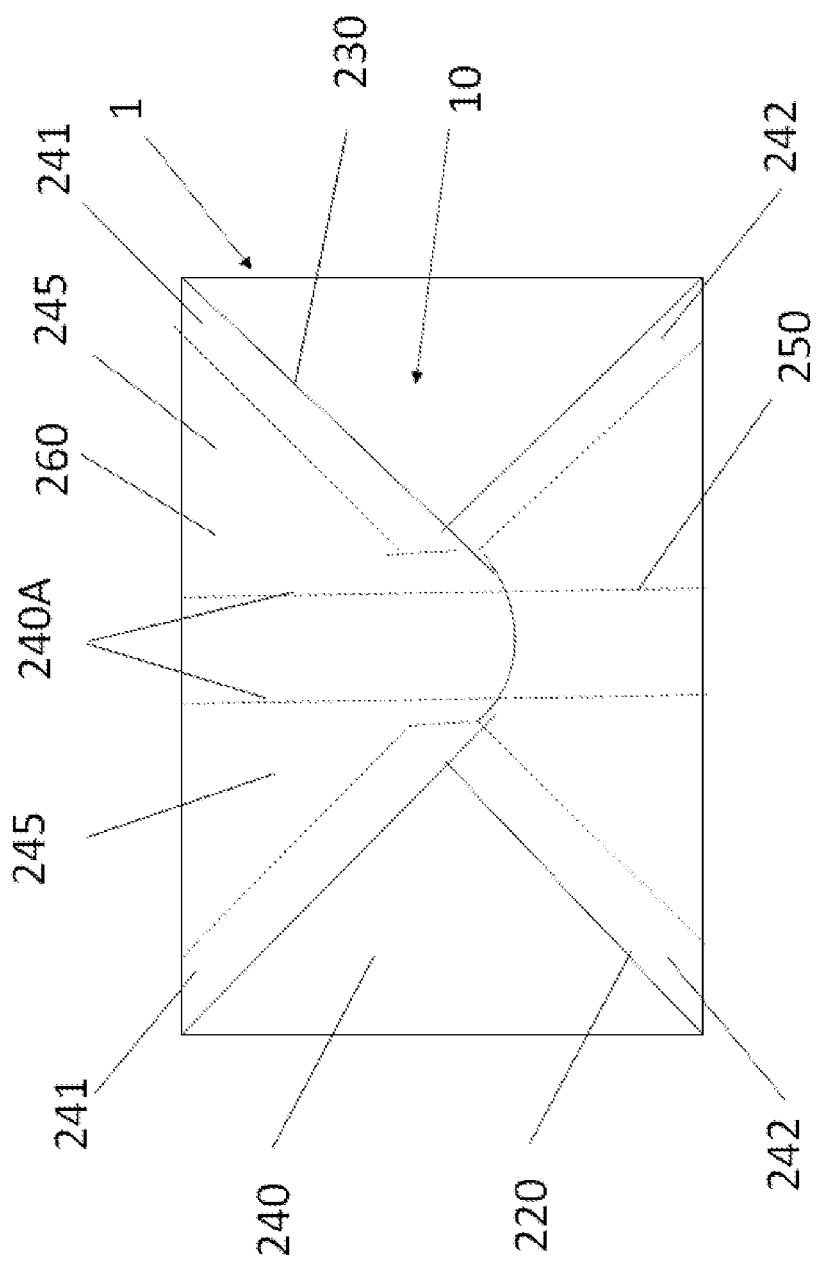
FIG. 2D is a schematic representation showing a panel of a package of the present disclosure, wherein the panel comprises seals in a block style configuration with seal areas identified.

Regarding FIG. 2D, recall that colorant coverage regarding seams/seals was mentioned. As shown in FIG. 2D, the base portion 240 may comprise inner edges 240A, seal areas 241 and 242, and colorant and coating free areas 245. As noted previously, in an effort to save on colorant weight percentage, it is contemplated that areas of the base portion 240 which are disposed under the first flap of package material 250 and second flap of package material 260 may be configured such that no colorants and/or coatings are provided in these areas. The exposed areas of the base portion 240 may comprise colorants and/or coatings. The seal areas 241 and/or 242 may be similarly configured as the colorant and coating free areas 245. Or, one or more of the seal areas 241 and 242 may comprise colorant and/or coating. And while a block style configuration is shown in FIG. 2D, the foregoing may be applied to cross style configurations as well.

Referring back to FIGS. 1C-1E, the bag 4 and package 1 dimensions may be suitably selected and effected through design, folding, stacking, compression and packaging processes so that the package 1 retains the absorbent articles therein and maintains a neat, stable, a substantially parallelepiped-shape, i.e. a cuboid shape of the package 1.

The first surface 10 may comprise the top panel of the package 1. Or the first surface 10 may comprise bottom panel of the package 1. It is worth noting that if the first surface 10 comprises seals, it may be desirable to make the first surface 10 comprise the bottom panel. In this way the seals may be hidden from view on the store shelf. Similarly, the second and third surfaces 12 and 13, as they may comprise gussets 12b and 13b, respectively, may comprise the left panel and right panel, respectively, or vice versa. Which leaves one of the fourth and fifth surfaces 14 and 15 to comprise the consumer-facing panel. So, at least one of the fourth and/or fifth surface 14, 15, may comprise branding, package information and/or background color as described herein. However, as noted previously, branding, package information, and/or background color is not limited to the consumer-facing panel. Any combination of the panels of the packages of the present disclosure may comprise branding, package information, and/or background color.

Figure 3A:
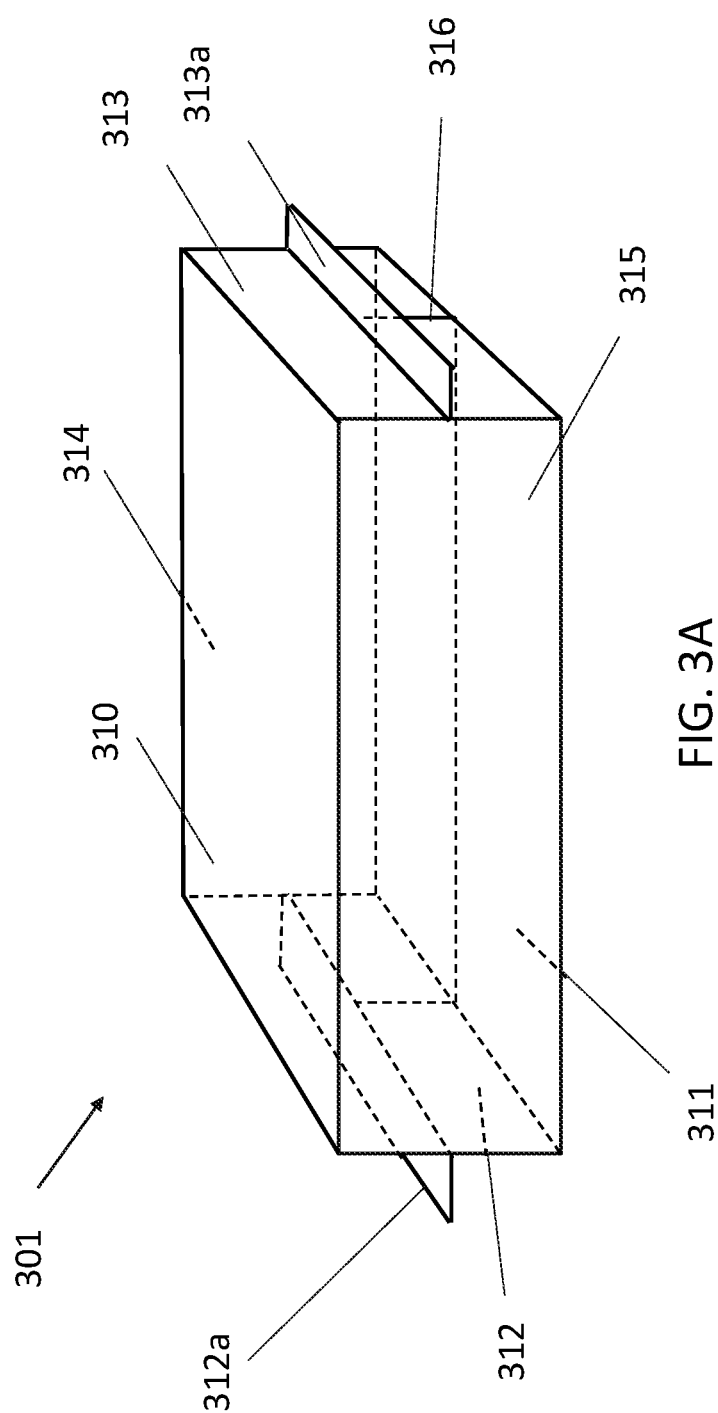
FIG. 3A is a schematic representation showing a package in accordance with the present disclosure constructed via a flow wrap process.

Recall that the flow wrap package configuration was also discussed heretofore. Some examples of flow wrap packages are shown in FIGS. 3A and 3B. FIG. 3A shows an exemplary flow wrap package which comprises a generally cuboid shape. Cuboid-shaped packages were discussed heretofore. Package 301, as shown comprises a first panel 311, opposing second and third panels 312 and 313, respectively; opposing fourth and fifth panels 314 and 315, respectively, and a sixth panel 310 opposing the first panel 311. As shown, the second panel 312 may comprise an end seal 312a, and the third panel 313 may comprise an end seam 313a. A hoop seal 316 may be disposed, in part on the second panel 312, the third panel 313, and the sixth panel 310. In such configurations, either the first panel 311 or the fifth panel 315 may comprise the consumer-facing panel.

FIG. 3B shows another exemplary package 321 in accordance with the packages of the present disclosure. Much like package 301 of FIG. 3A, package 321 is a flow wrap configuration. As shown, package 328 comprises a first surface 324 and an opposing second surface 328. Rounded edges may be provided as a transition between the first surface 324 and the second surface 328. Or, one or more fold lines may be provided between the first surface 324 and the second surface 328. Package 321 may further comprise end seals 322 and 323, and a hoop seal 326 which may be disposed on the second surface 328. In such packages, the first surface 324 may comprise the consumer-facing panel.

Regarding both FIGS. 3A and 3B, while the packages shown, i.e. 301 and 321, comprise butt seals for the end seal, overlap seals may also be utilized. For example, one or more of the end seals 312a, 313a, 322, and 323 may comprise an overlap seal. Similarly, the hoop seal, i.e. 316 and 326, may comprise either a butt seal or an overlap seal.

Figure 4A:
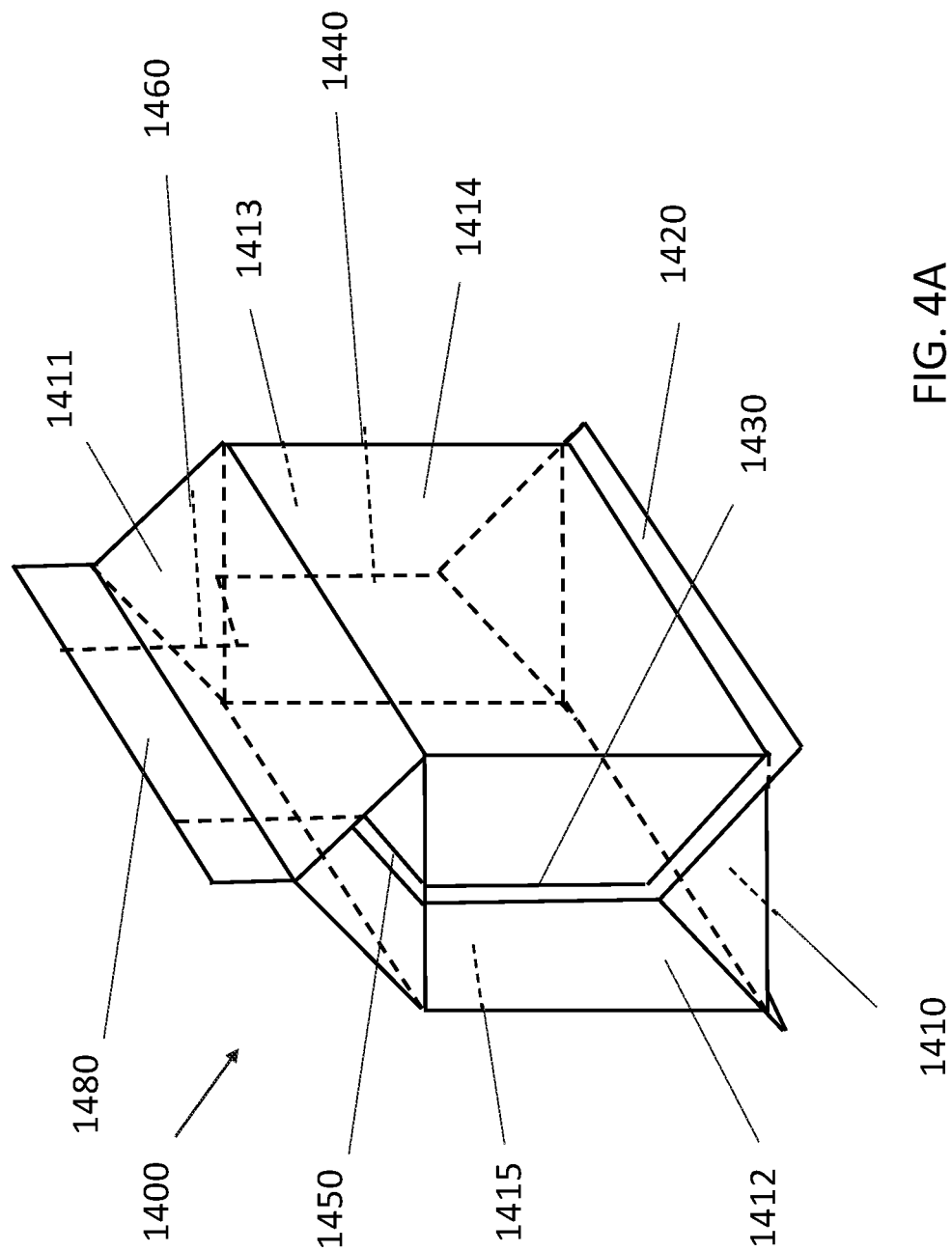
FIG. 4A is a schematic representation showing another package in accordance with the present disclosure constructed in accordance with the present disclosure.
Figure 4B:
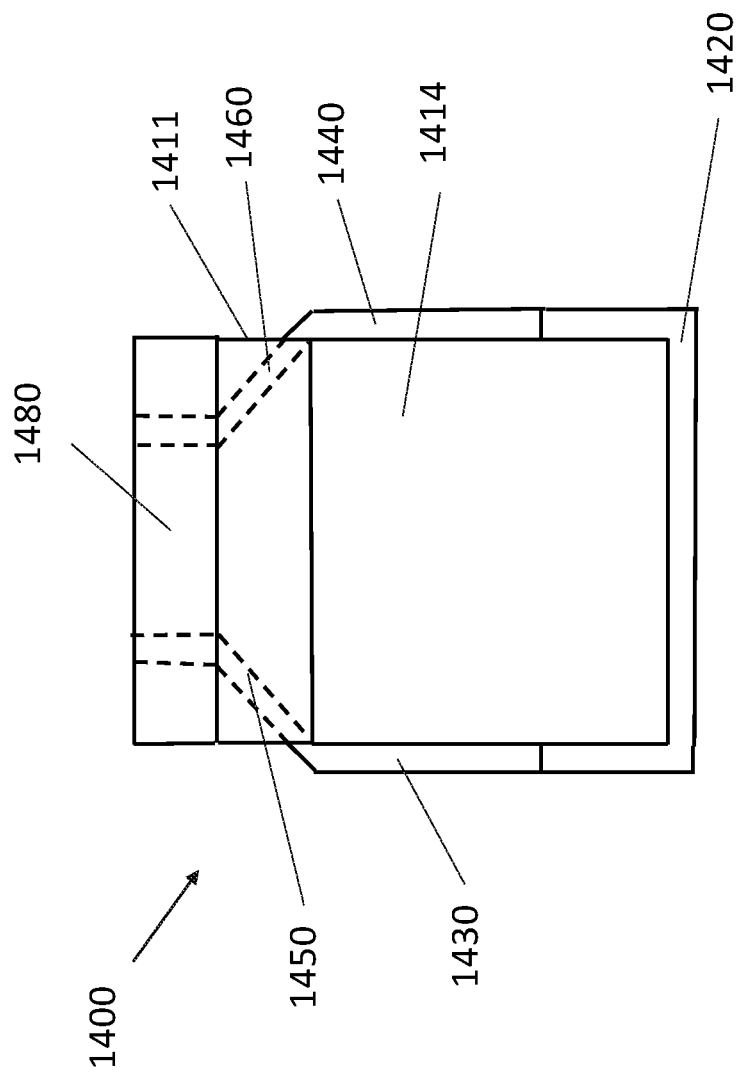
FIG. 4B is a schematic representation showing a rotated view of the package of FIG. 4A.

In yet another example, a Totani™ style bag may be utilized. The Totani™ style of bag may comprise seams/seals which are move overt than their block bottom, pinch bottom, and/or cross bottom counterparts. Referring to FIGS. 4A and 4B, a Totani™ style package 1400 is shown. The package 1400 may be configured in generally a cuboid shape. The package 1400 may comprise a first panel 1411, opposing second and third panels 1412 and 1413, opposing fourth and fifth panels 1414 and 1415, and a sixth panel 1410 opposing the first panel 1411. As shown, between the fourth panel 1414 and the sixth panel 1410, a first seal 1420 extends outward. The first seal 1420 forms a sort of foot for the package 1400. A second seal may extend outward between the fifth panel 1415 and the sixth panel 1410 in a similar fashion to the first seal 1420. It is worth noting that in some forms, the first panel 1411 may lay flat much like the sixth panel 1410.

The first seal 1420 can extend such that a portion of the first seal 1420 is on the second panel 1412 and another portion of the first seal 1420 is disposed on the third panel 1413. Similarly, a portion of the second seal may be disposed on the second panel 1412 and another portion may be disposed on the third panel 1413. The first seal 1420 and the second seal may be provided where the sixth panel 1410 is formed from a discrete piece of material which is subsequently joined to the fourth panel 1414 and fifth panel 1415. Of course forms where the sixth panel 1410 is unitary with the fourth panel 1414 and fifth panel 1415 are also contemplated.

A third seal 1430 and a fourth seal 1440 may extend outward from the second panel 1412 and the third panel 1413, respectively. It is worth noting that the first seal 1420, second seal, third seal 1430, and fourth seal 1440 collectively may comprise the hoop seal discussed heretofore. So, one, all or any combination, of these seals may exhibit the tensile strength for the hoop seal as described herein.

Figure 5:
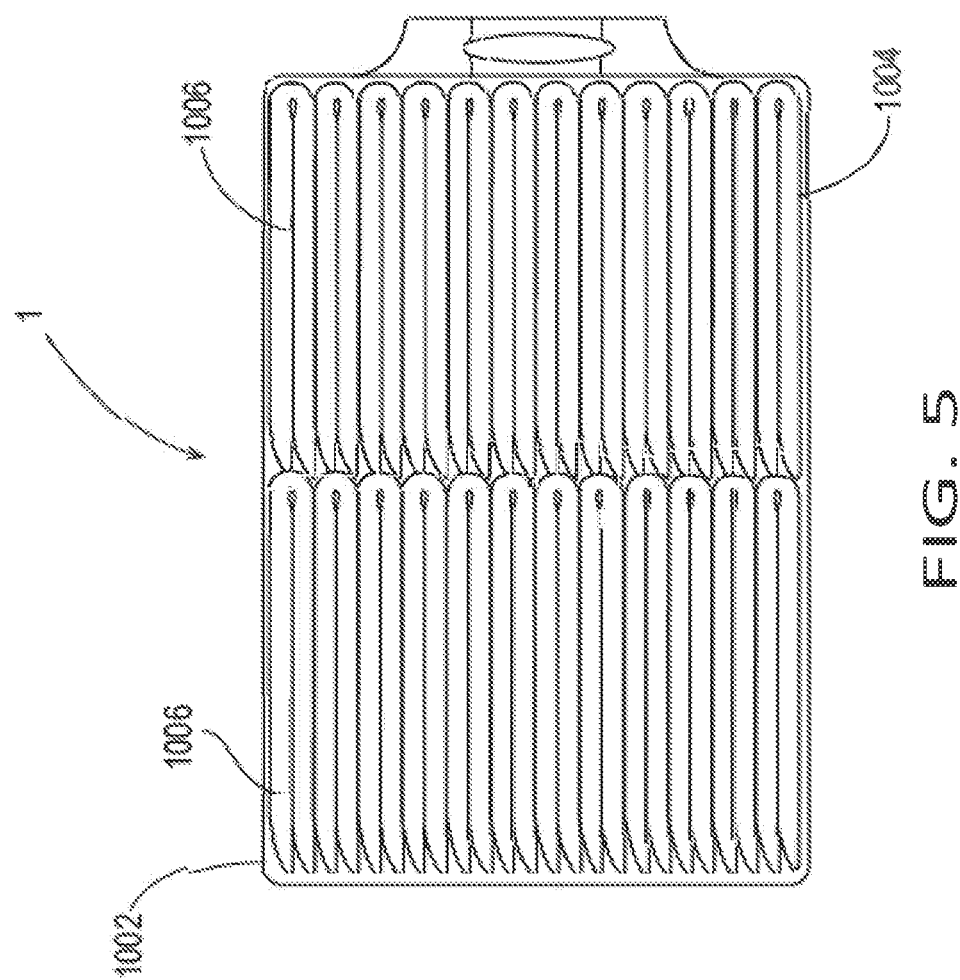
FIG. 5 is a cross-sectional view of the package of FIG. 1E showing absorbent articles therein.

As shown, the package 1400 may further comprise a fifth seam 1450 and a sixth seam 1460 which are disposed on the sixth panel 1411. The fifth seam 1450 and sixth seam 1460 can extend into a seal fin 1480. It is worth noting that the package 1400 and the seams associated therewith, may be assembled as described herein regarding adhesives, films, and/or combinations of films and adhesives. However, the construction of the package 1400 is particularly well suited for the creation of seams via film coating on an inner surface of the package material. In such configurations, the film may form a barrier that reduces the likelihood or at least the amount of moisture vapor through the package material to the absorbent articles therein. The packages of the present disclosure may comprise a plurality of compressed articles, e.g. compressed disposable absorbent articles. For example, packages of the present disclosure may be used for accommodating feminine hygiene pads. As shown in FIG. 5, the package 1 defines an interior space 1002 in which a plurality of absorbent articles 1004 are situated. The plurality of absorbent articles 1004 may be arranged in one or more stacks 1006. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. Despite lacking the stretch properties of conventional plastic packaging material, the inventors have surprisingly found the package materials of the present disclosure are able to withstand the processing and distribution rigors, as mentioned heretofore, even with absorbent articles which are compressed within the package. This is particularly unexpected as the materials of the present invention do not display the stretch properties of presently used conventional plastic films.

Accordingly, packages of the absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

It is worth noting that the absorbent articles within the packages of the present disclosure can be arranged in a myriad of configurations. For example, absorbent articles of the present disclosure may be disposed within the package such that they are oriented in a vertical orientation, or the absorbent articles may be arranged such that they are arranged in a horizontal configuration, for example as shown in FIG. 5. Forms are contemplated where a combination of horizontal and vertically oriented articles are provided in the package.

Additionally, the articles within the package may be oriented such that one longitudinal peripheral edge of each of the plurality of articles is more proximal to the consumer-facing panel than another longitudinal peripheral edge. For example, where the number of absorbent articles within the package is relatively high, e.g. greater than nine, the absorbent articles may be arranged within the package as described heretofore. However, where the number of absorbent articles within the package is lower than, for example nine, the absorbent articles may be arranged such that a topsheet or a backsheet of an absorbent article is more proximal to the consumer-facing panel. Additional absorbent articles may be stacked behind the absorbent article which is closest to the consumer-facing panel. Forms are contemplated where there is a combination of orientations within the package. For example, at least one absorbent article can be arranged such that one of its longitudinal peripheral side edges is more proximal the consumer-facing panel than another, and at least one absorbent article can be arranged such that its topsheet or backsheet is more proximal to the consumer-facing panel. The remainder of the absorbent articles, if any, can assume either of those configurations.

Absorbent Articles

Figure 6:
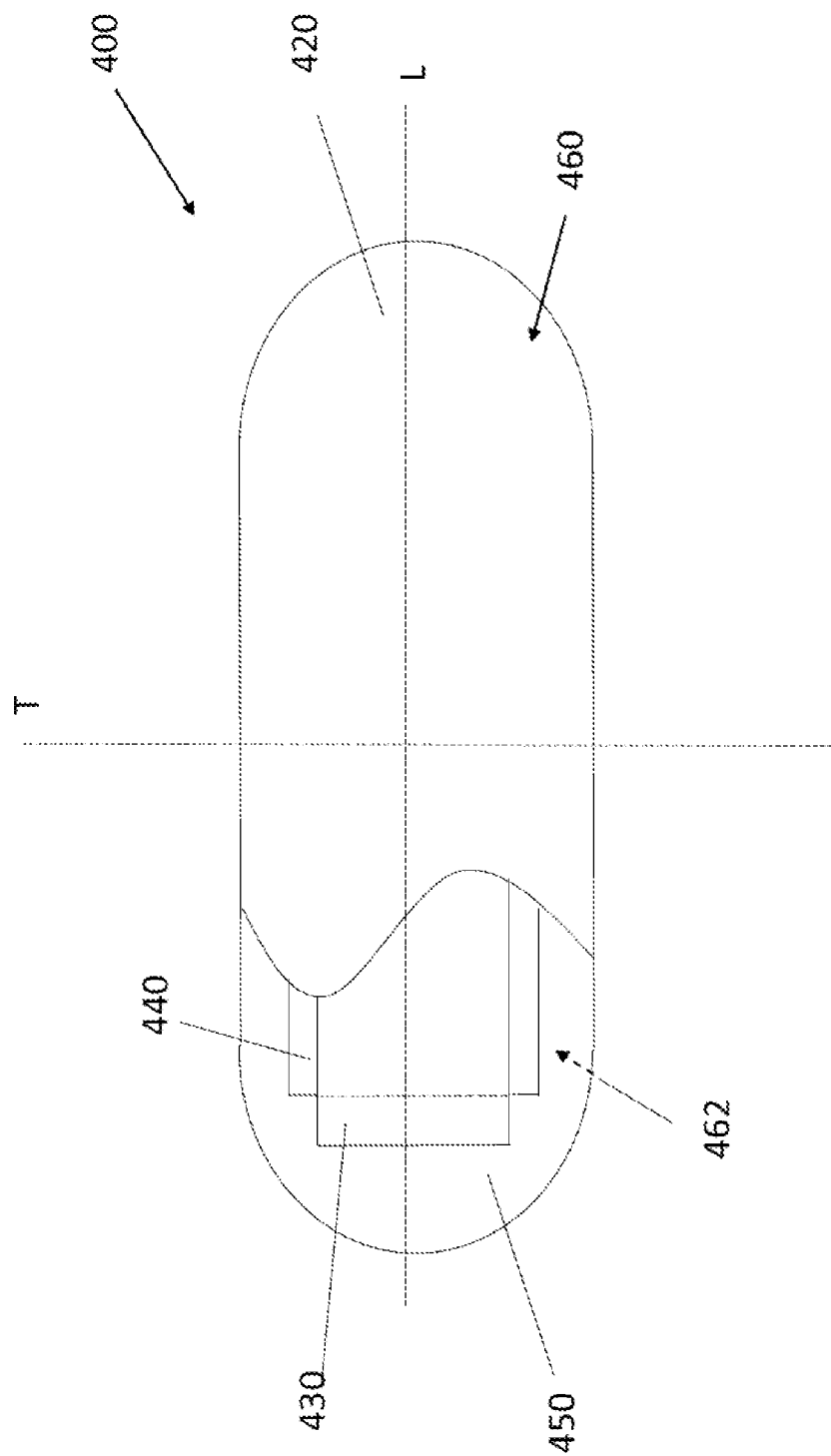
FIG. 6 is a schematic representation of an absorbent article of the present disclosure showing a partial-cutaway-view of the article.
Figure 7A:
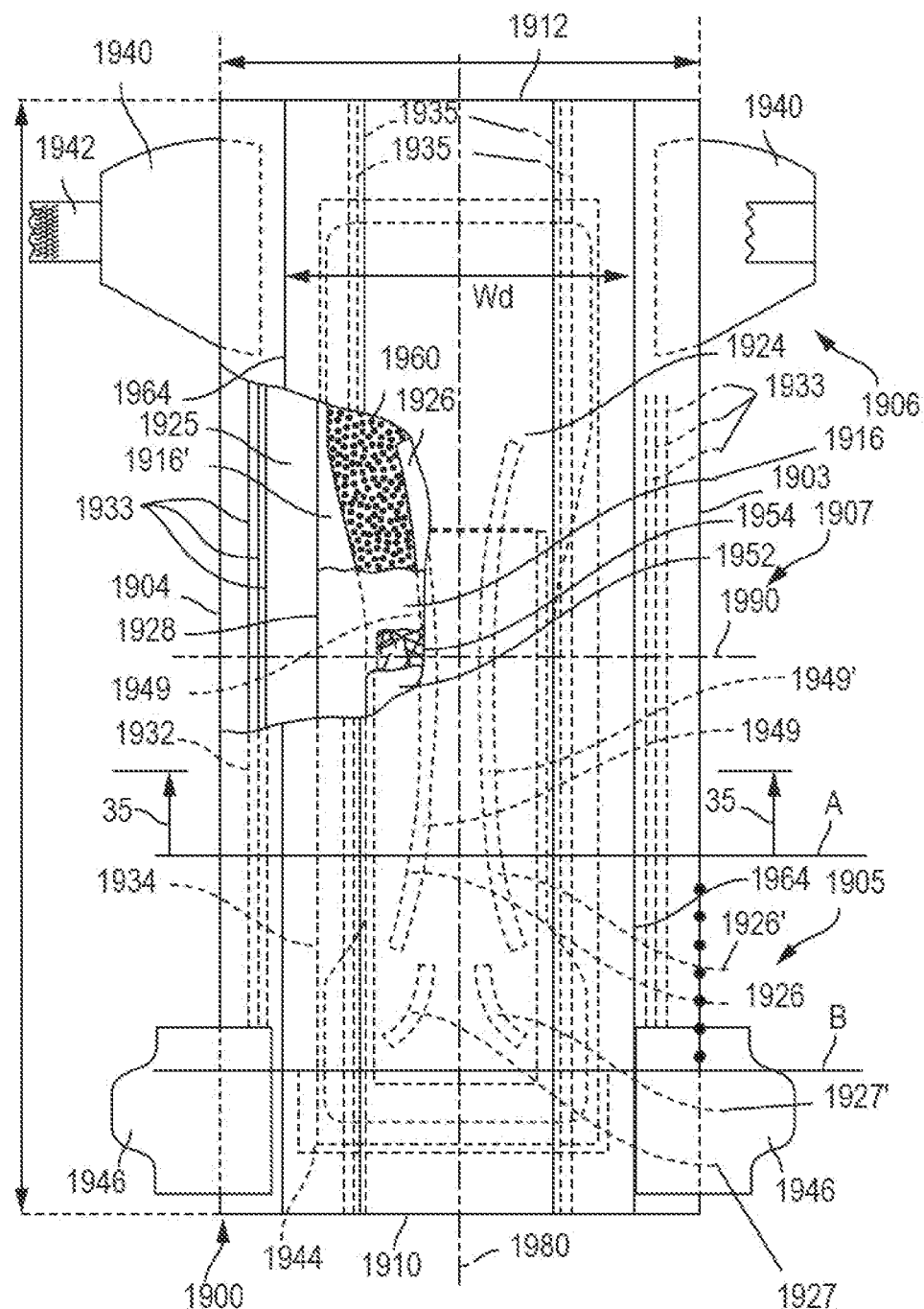
FIG. 7A shows a plan view of a diaper constructed in accordance with the present disclosure.
Figure 7B:
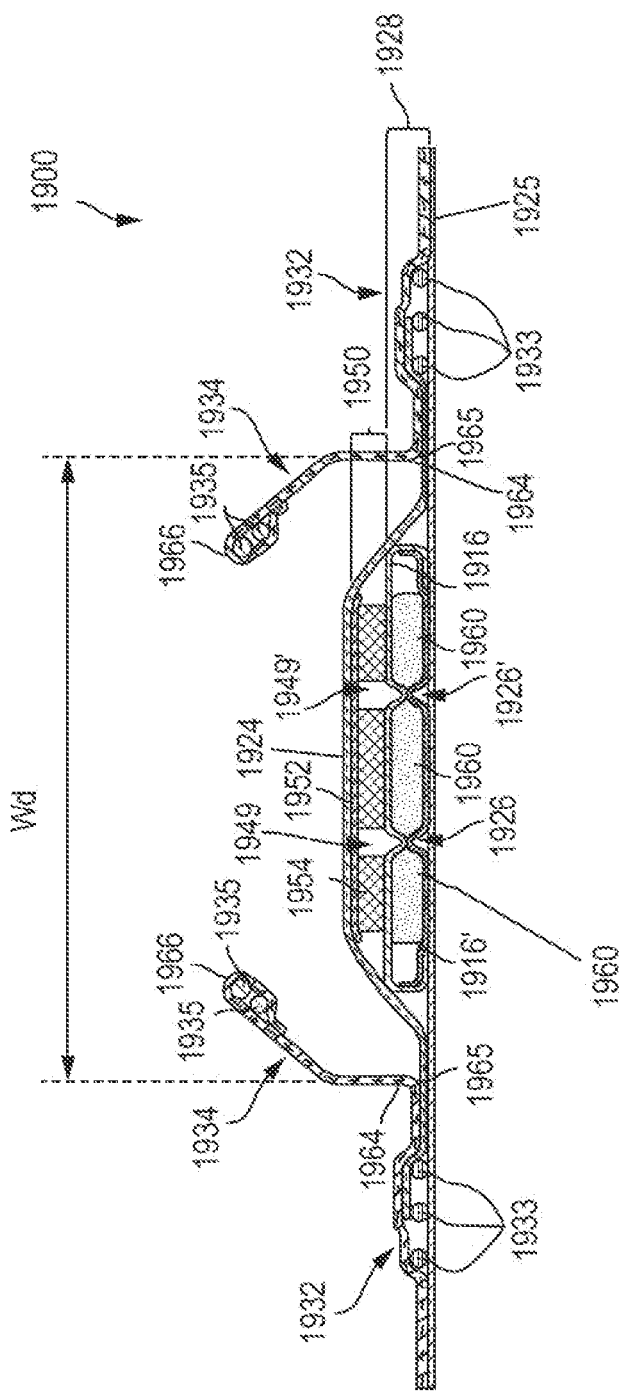
FIG. 7B shows a cross section of the diaper of FIG. 6A taken along lines 35-35.
Figure 7C:
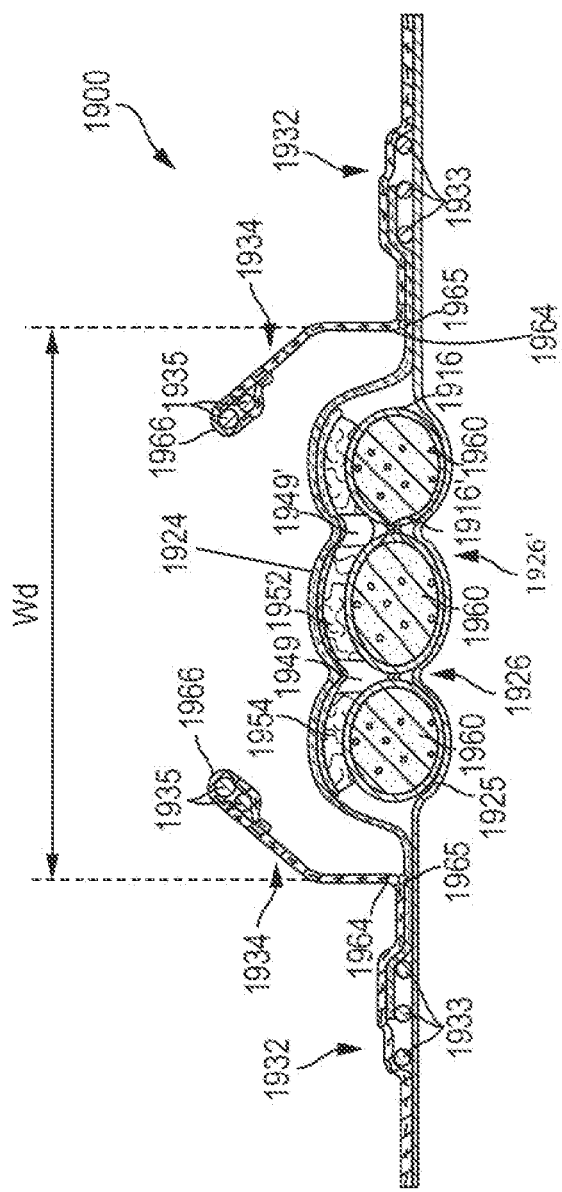
FIG. 7C shows a cross section of the diaper of FIG. 6B in an expanded state.

As noted previously, the absorbent articles which can be packaged within the package material of the present disclosure are numerous. Two specific examples are provided in FIGS. 6 through 7C. However, the package material and packages of the present disclosure may be utilized to contain a multitude of absorbent articles as described previously. FIGS. 6 through 7C are merely examples of articles which may be contained with the package material/packages of the present disclosure.

In FIG. 6 an exemplary feminine hygiene pad 400 is shown. The feminine hygiene pad 400 comprises a topsheet 420, a backsheet 450, and an absorbent core 440 disposed between the topsheet 420 and the backsheet 450. A fluid management layer 430 may be disposed between the topsheet 420 and the absorbent core 440. The absorbent article has a wearer-facing surface 460 and an opposing garment-facing surface 462. The wearer-facing surface 460 primarily comprises the topsheet 420 while the garment-facing surface 462 primarily comprises the backsheet 450. Additional components may be included in either the wearer-facing surface 460 and/or the garment-facing surface 462. For example, where the absorbent article is an incontinence pad, a pair of barrier cuffs which extend generally parallel to a longitudinal axis L of the absorbent article 400, may also form a portion of the wearer-facing surface 460. Similarly, a fastening adhesive may be present on the backsheet 450 and form a portion of the garment-facing surface 462 of the absorbent article.

The topsheet 420 may be joined to the backsheet 450 by attachment methods (not shown) such as those well known in the art. The topsheet 420 and the backsheet 450 may be joined directly to each other in the article periphery and may be indirectly joined together by directly joining them to the absorbent core 440, the fluid management layer 430, and/or additional layers disposed between the topsheet 420 and the backsheet 450. This indirect or direct joining may be accomplished by attachment methods which are well known in the art.

The topsheet 420 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 420 can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet include fibrous materials made from natural fibers, e.g. cotton, including 100 percent organic cotton, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, using any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 420 may be formed from a combination of an apertured film and a nonwoven. For example, a film web and a nonwoven web can be combined as described in U.S. Pat. No. 9,700,463. Alternatively, a film may be extruded onto a nonwoven material which is believed to provide enhanced contact between the film layer and the nonwoven material. Exemplary processes for such a combination are described in U.S. Pat. Nos. 9,849,602 and 9,700,463.

The backsheet 450 may be positioned adjacent a garment-facing surface of the absorbent core 440 and may be joined thereto by attachment methods such as those well known in the art. For example, the backsheet 450 may be secured to the absorbent core 440 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 450 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet may prevent, or at least inhibit, the exudates absorbed and contained in the absorbent core from wetting articles of clothing which contact the incontinence pad such as undergarments. However, the backsheet may permit vapors to escape from the absorbent core (i.e., is breathable) while in some cases the backsheet may not permit vapors to escape (i.e., non-breathable). Thus, the backsheet may comprise a polymeric film such as thermoplastic films of polyethylene or polypropylene. A suitable material for the backsheet is a thermoplastic film having a thickness of from about 0.012 mm (0.5 mil) to about 0.051 mm (2.0 mils), for example. Any suitable backsheet known in the art may be utilized with the present invention.

The backsheet 450 acts as a barrier to any absorbed bodily fluids that may pass through the absorbent core 440 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Exemplary backsheets are described in U.S. Pat. No. 5,885,265 (Osborn, III.) issued Mar. 23, 1999; U.S. Pat. No. 6,462,251 (Cimini) issued Oct. 8, 2002; U.S. Pat. No. 6,623,464 (Bewick-Sonntag) issued Sep. 23, 2003 or U.S. Pat. No. 6,664,439 (Arndt) issued Dec. 16, 2003. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may be a nonwoven web having a basis weight between about 20 gsm and about 50 gsm. As an example, the backsheet can be a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

The absorbent core 440 may comprise any suitable shape including but not limited to an oval, a discorectangle, a rectangle, an asymmetric shape, and an hourglass. For example, in some forms of the present invention, the absorbent core 440 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core may comprise varying stiffness in the MD and CD.

The configuration and construction of the absorbent core may vary (e.g., the absorbent core 440 may have varying caliper zones, a hydrophilic gradient, a superabsorbent gradient, or lower average density and lower average basis weight acquisition zones). Further, the size and absorbent capacity of the absorbent core 440 may also be varied to accommodate a variety of wearers. However, the total absorbent capacity of the absorbent core 440 should be compatible with the design loading and the intended use of the disposable absorbent article or incontinence pad.

In some forms of the present invention, the absorbent core may comprise a plurality of multi-functional layers that are in addition to the first and second laminates. For example, the absorbent core may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself. The absorbent core may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the core of the present disclosure are envisioned. In particular, potential additions to the current multi-laminate absorbent core are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described laminates of the absorbent core of the present invention. Additional examples of suitable absorbent cores are described in U.S. Patent Application Publication Nos. 2018/0098893 and 2018/0098891.

Any suitable fluid management layer may be utilized in conjunction with the feminine hygiene pad 400. The fluid management layer may be separate and apart from the absorbent system. Additionally, the fluid management layer is disposed beneath the topsheet and on the wearer-facing surface of the core. The fluid management layer may have a basis weight from about 40 gsm to about 100 gsm, from about 45 gsm to about 75 gsm, or from about 50 gsm to about 65 gsm, specifically including all values within these ranges and any ranges created thereby. In some forms, the fluid management layer may comprise a homogeneous mix of fibers whereas in other forms, the fluid management layer may comprise a heterogeneous mix of fibers.

Some exemplary fluid management layers are described in U.S. Patent Application Publication Nos. 2015/0351976 A1 and 2014/0343523 A1; and U.S. patent application Ser. No. 15/729,704.

Another example of an absorbent article which can be included in the packages of the present disclosure are diapers. As shown in FIG. 7A, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the packages of the present disclosure may be used for a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 7B), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1920 and cooperating with a landing zone 1944 on the front of the absorbent article 1920. The absorbent article may also comprise other typical elements, which are not represented, such as a rear elastic waist feature and a front elastic waist feature, for example.

The absorbent article 1920 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1920 which is intended to be placed towards the front of the user when worn, and the rear waist edge 1912 is the opposite edge. Together the front waist edge 1910 and the rear waist edge form waist opening when the absorbent article 1920 is donned on a wearer. The absorbent article 1920 may have a longitudinal axis 1980 extending from the lateral midpoint of the front waist edge 1910 to a lateral midpoint of the rear waist edge 1912 of the absorbent article 1920 and dividing the absorbent article 1920 in two substantially symmetrical halves relative to the longitudinal axis 1980, with article placed flat and viewed from the wearer-facing surface as illustrated FIG. 7A. The absorbent article may also have a lateral axis 1990 extending from the longitudinal midpoint of the first side edge 1903 to the longitudinal midpoint of the second side edge 1904. The length L of the absorbent article 1920 may be measured along the longitudinal axis 1980 from the front waist edge 1910 to the rear waist edge 1912. The crotch width of the absorbent article 1920 may be measured along the lateral axis 1990 from the first side edge 1903 to the second side edge 1904. The absorbent article 1920 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

The absorbent core 1928 may comprises one or more channels, represented in FIG. 7A as the four channels 1926, 1926' and 1927, 1927'. Additionally or alternative, the LMS 1950 may comprises one or more channels, represented in FIGS. 7A-7C as channels 1949, 1949'. In some forms, the channels of the LMS 1950 may be positioned within the absorbent article 1920 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1920.

The backsheet 1925 is generally that portion of the absorbent article 1920 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm Example backsheet films include those manufactured by Tredegar Corporation, based in Richmond, VA, and sold under the trade name CPC2 film. Other suitable backsheet materials may include breathable materials which permit vapors to escape from the absorbent article 1920 while still preventing, or at least inhibiting, bodily exudates from passing through the backsheet 1925. Example breathable materials may include materials such as woven webs, nonwoven webs, and composite materials such as film-coated nonwoven webs, microporous films, and monolithic films.

The backsheet 1925 may be joined to the topsheet 1924, the absorbent core 1928, and/or any other element of the absorbent article 1920 by any attachment methods known to those of skill in the art. Suitable attachment methods are described above with respect to methods for joining the topsheet 1924 to other elements of the absorbent article 1920.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 7A. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer 1961 of absorbent material, which may be 100% or less of SAP. The second absorbent layer may comprise the second material 1916' and a second layer 1962 of absorbent material, which may also be 100% or less of SAP.

The fibrous thermoplastic adhesive material 1951 may be at least partially in contact with the absorbent material 1961, 1962 in the land areas and at least partially in contact with the materials 1916 and 1916' in the junction areas. This imparts an essentially three-dimensional structure to the fibrous layer of thermoplastic adhesive material 591, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal for the core wrap does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 1964 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal. It is worth noting that barrier leg cuffs may similarly be applied to a pad type of structure as described regarding FIG. 6. Such configurations may be desirable in an adult incontinence pad. Any of the configurations described herein for the barrier leg cuffs may be utilized for adult incontinence pads.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 7A, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise two layers: a distribution layer 1954 and an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Grad), for example.

The LMS 1950 may comprise a distribution layer 1954. The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 1950 may alternatively or additionally comprise an acquisition layer 1952. The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1920 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Arrays of Packages

With the package material of the present disclosure, it is contemplated that a wide variety of packaging arrays may be provided to address the concerns of a variety of consumers. As an example, the packages of the present disclosure may be utilized with absorbent articles which have more components which are natural or have natural components. For example, the packages of the present disclosure may be utilized with absorbent articles which include a cotton topsheet and/or a cotton based fluid management layer or acquisition layer. Additionally or alternatively, the packages of the present disclosure can be utilized with absorbent articles which are unscented and/or have unbleached pulp in their absorbent cores.

While some of the absorbent article offerings may be in the packages of the present disclosure, other of the absorbent article offerings may be in conventional packaging. However, in an effort to drive more sustainable manufacturing practices, it is contemplated of the absorbent articles offered by a single manufacturer of absorbent articles on a store shelf, that at least 20 percent comprise recyclable packages as described herein, at least 40 percent, or at least 50 percent, specifically reciting all values within these ranges or any ranges created thereby. For example, where a manufacturer of absorbent articles has 5 absorbent article offerings on a store shelf, e.g. 2 diapers sizes, 3 feminine hygiene pad sizes, at least one of the packages for a single diaper size or a single feminine hygiene pads size may comprise recyclable packaging as described herein.

Arrays are contemplated where the package material of the present disclosure is utilized for two different absorbent articles and wherein the packages have a different seal configuration. For example, a first package may comprise a plurality of feminine hygiene pads and comprise at least one panel having a block style configuration. A second package may comprise a plurality of diapers and comprise at least one panel having a pinch style or cross style configuration.

Test Methods

ASTM F88-06—Seal Tensile Strength

This test method determines the strength of a seal in flexible barrier materials by measuring the force required to separate a test strip of material containing the seal. Seal strength is measured in accordance with compendial method ASTM F0088-06 on a constant rate of extension tensile tester, with procedural specifics noted herein. A suitable instrument is the Instron Model 5965 using Bluehill Universal Software, both available from Instron Norwood, MA), or equivalent. All measurements are performed in a laboratory maintained at 23° C.±2° C. and 50%±2% relative humidity and test samples are conditioned in this environment for 2 hours prior to testing.

The preparation of the test specimens and test procedure is described in the referenced ASTM method, with the following specific details. The test specimen is cut to a width of 1.0 inch, the grip separation rate is 300 mm/min, and the tail-holding method is unsupported. The maximum force encountered as the test specimen is stressed to failure is recorded as force per unit width to the nearest 0.1 N/in. The test is repeated for a total of five replicate test specimens. Calculate the arithmetic mean for maximum seal strength and report as Tensile Strength to the nearest 0.1 N/in.

ISO 1924-3—Tensile Properties (Tensile Strength, Stretch, Energy Absorption)

The tensile properties (tensile strength, stretch and energy absorption) of a test sample are calculated from measured force and elongation values obtained using a constant rate of elongation test until the sample breaks. The test is run in accordance with compendial method ISO 1924-3, with modifications noted herein. Measurements are made on a constant rate of extension tensile tester using a load cell for which the forces measured are within 1% to 99% of the limit of the cell. A suitable instrument is the MTS Alliance using Test Suite Software, available from MTS Systems Corp., Eden Prairie, MN, or equivalent. All measurements are performed in a laboratory maintained at 23° C.±2° C. and 50%±2% relative humidity and test samples are conditioned in this environment for at least 2 hours prior to testing.

Measurements are made on both MD (machine direction) and CD (cross direction) test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is cut to a width of 25.4 mm with a length that can accommodate a test span of 50.8 mm. The long side of the sample is parallel to the direction of interest (MD, CD). Normally in finished packages, the MD runs from the bottom to the top of the package, but this can be verified by determining the fiber orientation if in doubt. Ten replicate test samples should be prepared from the MD and ten additional replicates from the CD.

Program the tensile tester for a constant rate of extension uniaxial elongation to break as follows. Set the gauge length (test span) to 50.8 mm using a calibrated gauge block and zero the crosshead. Insert the test sample into the grips such that the long side is centered and parallel to the central pull axis of the tensile tester. Raise the crosshead at a rate of 25.4 mm/min until the test sample breaks, collecting force (N) and extension (mm) data at 100 Hz throughout the test. Construct a graph of force (N) versus extension (mm). Read the maximum force (N) from the graph and record as Peak Force to the nearest 0.1 N, noting MD or CD. Read the extension at the maximum force (N) from the graph and record as Elongation at Break to the nearest 0.01 mm, noting MD or CD. From the graph, determine the point (z) where the tangent to the curve, with a slope equal to the maximum slope of the curve, intersects the elongation axis. Now calculate the area under the force vs elongation curve from point z up to the point of maximum force and report to the nearest 0.1 mJ, noting MD or CD. [Refer to Figure 2 in ISO 1924-3 for a depiction of a typical force vs elongation curve where point z is denoted.]

Calculate the arithmetic mean Peak Force for all MD replicates and then all CD replicates and record respectively as Mean MD Peak Force and Mean CD Peak Force to the nearest 0.1 N. Calculate the arithmetic mean Elongation at Break for all MD replicates and then all CD replicates and record respectively as Mean MD Elongation at Break and Mean CD Elongation at Break to the nearest 0.01 mm Calculate the arithmetic mean area under the force vs elongation curve for all MD replicates and then all CD replicates and record respectively as Mean Area Under MD Curve and Mean Area Under CD Curve to the nearest 0.1 mJ.

Tensile strength is calculated by dividing the Mean Peak Force (N) by the width of the test sample (25.4 mm). Calculate the tensile strength for the MD replicates and then the CD replicates and report respectively as MD Tensile Strength and CD Tensile Strength to the nearest 0.1 kN/m.

Stretch at break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

ISO 2758—Burst Strength

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23° C.+/−2° C. and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

ISO 534—Caliper

The caliper, or thickness, of a single-layer test sample is measured under a static load by a micrometer, in accordance with compendial method ISO 534, with modifications noted herein. All measurements are performed in a laboratory maintained at 23° C.±2° C. and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm² and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

ISO 536—Basis Weight

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 5). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm Percentage of Colorant Coverage Measurement Method The Percentage of Colorant Coverage measurement method measures the percent area of colorant coverage on a package panel. A flatbed scanner capable of scanning a minimum of 24 bit color at 800 dpi with manual control of color management (a suitable scanner is an Epson Perfection V750 Pro from Epson America Inc., Long Beach CA, or equivalent) is used to acquire images. The scanner is interfaced with a computer running color calibration software capable of calibrating the scanner against a color reflection IT8 target utilizing a corresponding reference file compliant with ANSI method IT8.7/2-1993 (suitable color calibration software is Monaco EZColor or i1Studio available from X-Rite Grand Rapids, MI, or equivalent). The color calibration software constructs an International Color Consortium (ICC) color profile for the scanner, which is used to color correct an output image using an image acquisition program that supports application of ICC profiles. The color corrected image is then segmented via color thresholding using color analysis software (a suitable image color analysis software is MATLAB R2017b available from The Mathworks, Inc., Natick, MA).

The samples are conditioned at about 23° C.±2° C. and about 50%±2% relative humidity for 2 hours prior to testing.

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for a scanner, which will be applied within the image analysis program to correct the color of subsequent output images.

A sample is obtained from a package or package materials with identified panels. A single panel is selected and cut along its perimeter to remove it for testing. Panels selected for testing should not contain tears or wrinkles.

The scanner lid is opened, and the sample carefully laid flat on the center of the scanner glass with the colored surface oriented toward the glass. A scan containing a panel region is acquired at 24 bit color with a resolution of 800 dpi (approximately 31.5 pixels per mm) in reflectance mode. The ICC color profile is assigned to the image producing a color corrected sRGB image. This calibrated image is saved in an uncompressed format to retain the calibrated R,G,B color values, such as a TIFF file, prior to analysis.

The calibrated image is opened in the color analysis software. The image is smoothed using a 2D Gaussian filter with a sigma of 3 to blur out any individual dots of colorant. Next, utilizing a color thresholding program, a color space to perform the color thresholding is selected, for example CIELAB with its three color values L*,a*,b*. Then a region of interest (ROI) boundary is manually drawn within a visibly discernable region of only the base color, without any colorants present, to identify its color space values. A panel with no visible base color region will be deemed to have 100% colorant coverage. The thresholding levels in all three channels of the selected color space are then manually adjusted to segment the regions of the panel that contain colorant coverage from those regions of the base color. The area of the panel containing colorant coverage is measured and the percentage of the area of the panel containing colorant coverage is calculated and recorded to the nearest whole percent.

In like manner, prepare, scan and analyze six replicate package panels. Calculate and report the arithmetic mean of the measured percent area of colorant coverage values to the nearest whole percent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package of one or more absorbent articles, the package comprising a package material, wherein the package material comprises natural fibers, wherein the package comprises a plurality of panels, including a consumer-facing panel, wherein the package is sealed such that the one or more absorbent articles are enclosed therein, wherein the package material comprises a basis weight of between 50 gsm to 120 gsm, wherein the package material is recyclable, and wherein the package exhibits a recyclable percentage of between about 70 percent to about 99.9 percent as determined by the PTS-RH:021/97 (Draft October 2019), under category II, test method.

2. The package of claim 1, wherein the package material comprises between 50 and 100 percent by weight of natural fibers.

3. The package of claim 1, wherein the natural fibers of the packaging material comprise at least one of: cellulose-based fibers, bamboo based fibers, cotton, abaca, kenaf, sabai grass, flax, esparto grass, straw, jute hemp, bagasse, milkweed floss fibers, pineapple leaf fibers, wood fibers, or pulp fibers.

4. The package of claim 1, wherein the natural fibers comprise at least one of wood fibers or pulp fibers.

5. The package of claim 1, wherein the package material comprises recycled natural fibers as determined via visual inspection utilizing the human eye and/or microscopy.

6. The package of claim 1, wherein at least one of the plurality of panels comprises a background color, branding, and/or package information.

7. The package of claim 6, wherein the at least one of the plurality of panels comprises a percentage of colorant coverage of 75 percent or less.

8. The package of claim 1, wherein the consumer-facing panel comprises a base color.

9. The package of claim 8, wherein the one or more absorbent articles are natural based.

10. The package of claim 1, wherein the consumer-facing panel comprises a first colorant coverage percentage which is greater than a second colorant coverage percentage of another panel of the package.

11. The package of claim 1, wherein the package comprises a plurality of seals, wherein each of the plurality of seals has a tensile strength of at least 3 N/in.

12. The package of claim 11, wherein at least one of the plurality of seals has a higher tensile strength than another of the plurality of seals.

13. The package of claim 11, wherein at least one of the plurality of seals has a tensile strength of from between 15N/in to about 40 N/in.

14. The package of claim 13, wherein the one or more absorbent articles within the package comprise diapers or adult incontinence pants.

15. The package of claim 11, wherein the tensile strength of at least one seal of the package is from about 3 N/in to about 25 N/in.

16. The package of claim 15, wherein the one or more absorbent articles comprise at least one of menstrual pads, light adult incontinence pads, and liners.

17. The package of claim 11, wherein at least one of the seals comprises a dissolvable adhesive or a dispersible adhesive.

18. The package of claim 1, wherein the package comprises non-recyclable material having a weight percentage of from between about 0.1 percent to about 30 percent.

19. The package of claim 1, wherein the package comprises non-recyclable material having a weight percentage of from between 0.1 to about 5 percent by weight.

20. The package of claim 16, wherein the package material does not comprise a barrier layer.

21. The package of claim 14, wherein the package material comprises a barrier layer.

22. A package of one or more absorbent articles, the package comprising a package material, wherein the package material comprises natural fibers, wherein the package comprises a plurality of panels, including a consumer-facing panel, wherein the package is sealed such that the one or more absorbent articles are enclosed therein, wherein the package material comprises a basis weight of between 50 gsm to 120 gsm, wherein the package material is recyclable, and wherein the package comprises non-recyclable material having a weight percentage of from between, from about 0.1 percent to about 30 percent.

* * * * *